(12) United States Patent
Royce et al.

(10) Patent No.: US 12,711,831 B2
(45) Date of Patent: Aug. 18, 2026

(54) MEDICATION DOCUMENTATION PREPARATION SYSTEM AND APPARATUS

(71) Applicant: Innovation Associates, Inc., Johnson City, NY (US)

(72) Inventors: David Royce, Johnson City, NY (US); Ryan Van Tassel, Johnson City, NY (US); Nicholas Twining, Johnson City, NY (US); Conner Sweeney, Johnson City, NY (US); Eric Shelley, Johnson City, NY (US)

(73) Assignee: Innovation Associates, Inc., Binghamton, NY (US)

( * ) Notice: Subject to any disclaimer, the term of this patent is extended or adjusted under 35 U.S.C. 154(b) by 282 days.

(21) Appl. No.: 18/429,880

(22) Filed: Feb. 1, 2024

(65) Prior Publication Data

US 2024/0257600 A1 Aug. 1, 2024

Related U.S. Application Data

(60) Provisional application No. 63/442,521, filed on Feb. 1, 2023.

(51) Int. Cl.

| | |
|---|---|
| ***G16H 20/13*** | (2018.01) |
| ***G07F 17/00*** | (2006.01) |
| *B65B 9/02* | (2006.01) |
| *B65B 15/00* | (2006.01) |
| *B65B 41/02* | (2006.01) |

(52) U.S. Cl.
CPC ......... *G07F 17/0092* (2013.01); *G16H 20/13* (2018.01); *B65B 9/02* (2013.01); *B65B 15/00* (2013.01); *B65B 41/02* (2013.01)

(58) Field of Classification Search
CPC ....... G07F 17/0092; G16H 20/13; B65B 9/02; B65B 15/00; B65B 41/02
See application file for complete search history.

(56) References Cited

U.S. PATENT DOCUMENTS

| | | | |
|---|---|---|---|
| 4,899,520 A | | 2/1990 | Lerner et al. |
| 5,221,567 A | | 6/1993 | Baker |
| 5,417,041 A | | 5/1995 | Hansen et al. |
| 5,568,718 A | | 10/1996 | Lerner et al. |
| 5,687,545 A | | 11/1997 | Baker |
| 5,771,657 A | * | 6/1998 | Lasher .................... B65B 61/20 53/493 |
| 5,918,441 A | | 7/1999 | Baker |
| 6,145,273 A | | 11/2000 | Baker |
| 6,351,926 B1 | | 3/2002 | Hodge et al. |
| 6,419,392 B1 | | 7/2002 | Baker |
| 6,470,648 B1 | | 10/2002 | Baker |
| 6,543,201 B2 | | 4/2003 | Cronauer et al. |

(Continued)

FOREIGN PATENT DOCUMENTS

CA 2853250 A1 * 5/2013 ............. G16H 20/13

*Primary Examiner* — Justin Holmes
(74) *Attorney, Agent, or Firm* — K&L Gates LLP

(57) ABSTRACT

A medication documentation preparation system is disclosed. Medication documentation is printed and deposited into a tray where the medication documentation is verified by one or more scanners. If the medication documentation has been correctly printed, the medication documentation is folded and transported by a gantry assembly to be packaged. If the medication documentation has not been printed correctly, it is rejected and the process begins again.

20 Claims, 27 Drawing Sheets

(56) References Cited

U.S. PATENT DOCUMENTS

| | | | | |
|---|---|---|---|---|
| 6,742,317 | B2 | 6/2004 | Cronauer et al. | |
| 6,827,490 | B2 | 12/2004 | Baker | |
| 7,258,656 | B2 | 8/2007 | Lerner et al. | |
| 7,448,185 | B2 | 11/2008 | Zeedyk et al. | |
| 7,552,571 | B2 | 6/2009 | Lerner et al. | |
| 7,571,584 | B2 | 8/2009 | Lerner et al. | |
| 7,654,064 | B2 | 2/2010 | Riccardi et al. | |
| 7,757,459 | B2 | 7/2010 | Wehrmann | |
| 7,794,380 | B2 | 9/2010 | Baker | |
| 7,897,219 | B2 | 3/2011 | Wehrmann | |
| 8,069,635 | B2 | 12/2011 | Riccardi et al. | |
| 8,141,329 | B2 | 3/2012 | Zeedyk et al. | |
| 8,307,617 | B2 | 11/2012 | Riccardi et al. | |
| 8,549,822 | B2 | 10/2013 | Lerner et al. | |
| 8,887,978 | B2 | 11/2014 | Chuba | |
| 8,986,476 | B2 * | 3/2015 | Dent | G16H 40/60<br>156/DIG. 47 |
| 9,617,102 | B2 | 4/2017 | Chuba | |
| 10,336,489 | B2 | 7/2019 | Riccardi et al. | |
| 10,730,260 | B2 | 8/2020 | Wehrmann | |
| 11,001,401 | B2 | 5/2021 | Riccardi et al. | |
| 11,040,793 | B2 | 6/2021 | Riccardi et al. | |
| 11,325,733 | B2 | 5/2022 | Shook et al. | |
| 2014/0116010 | A1 | 5/2014 | Baker | |
| 2021/0284372 | A1 | 9/2021 | Riccardi et al. | |
| 2022/0009090 | A1 * | 1/2022 | Morikubo | B65B 17/00 |
| 2022/0112015 | A1 | 4/2022 | Berguig | |
| 2022/0258899 | A1 | 8/2022 | Shook et al. | |

* cited by examiner

MEDICATION DOCUMENTATION PREPARATION SYSTEM AND APPARATUS

PRIORITY CLAIM

This application claims priority to and the benefit of U.S. Provisional Patent Application Ser. No. 63/442,521, filed on Feb. 1, 2023, the entire disclosure of which is hereby incorporated by reference.

BACKGROUND

Typical prescription medication fulfillment systems process hundreds to thousands of prescriptions a day. These prescription medication fulfillment systems may be used for the online fulfillment of medication prescriptions in instances where patient-specific local pharmacy preparation is not needed. Additionally, some prescription medication fulfillment systems may use conveyance systems to at least help automate operations that may instead be performed a local pharmacies, such as prescription filling and packaging.

One type of medication fulfillment consists of placing a medication container and corresponding documentation into a bag for shipment. Currently, placement of the medication container into the bag is a semi-automated process. A conveyor system routes a medication container to a packing station. An operator then manually picks up and places the medication container into a bag or other receptacle. The operator also then retrieves medication documentation from a printer, folds the documentation, and places the documentation into the bag. The operator then seals the bag and places a printed label on the bag for shipping. The operator then places the bag into a tote that is routed to a shipping department.

The above process is relatively time intensive and operator intensive. For a facility that processes thousands of orders a day, at least eight to ten operators are needed to manually package single medication containers into bags. While some parts of the process are automated, such as the medication container routing, documentation printing, bag preparation, and label printing, other parts of the process including the aggregation and bagging of the order are labor intensive.

In addition, it is critical that the fulfillment process be accurate. If a patient receives incorrect medication, the results could be disastrous or even deadly for the patient. Even medication of the same compound can be made in different dosage levels which can cause negative effects in a patient that ingests the wrong dosage. For this reason, extra care is put into medication fulfillment.

A need accordingly exists for a single, modular pharmacy automation machine that automatically packages single medication containers.

Additionally, a need exists for an accurate and efficient machine to assist with medication fulfillment.

SUMMARY

Example systems, methods, and apparatus are disclosed herein for bagging single medication containers and corresponding documentation.

In light of the disclosure herein and without limiting the disclosure in any way, in an aspect of the present disclosure, which may be combined with any other aspect listed herein unless specified otherwise, an infeed loop apparatus for a medication bagger system includes at least one feed transport mechanism including an input end configured to receive at least one medication container and an exit end connected to a dispensing mechanism. Additionally, the infeed loop apparatus includes at least one diverter transport mechanism which includes a first end connected to the exit end of the feed transport mechanism, and a second end connected to the input end of the feed transport mechanism. The infeed loop apparatus also includes an output transport mechanism configured to dispense the medication container from the feed transport mechanism, a scanner located along a portion of the input end of the feed transport mechanism or the diverter transport mechanism, the scanner configured to read a label on the medication container to obtain label patient information, and a router connected to the exit end of the feed transport mechanism and the first end of the diverter transport mechanism, the router configured to selectively route the medication container to the output transport mechanism or the diverter transport mechanism based on the label patient information from the scanner matching patient information stored in a fulfillment database indicative as to whether the medication container is ready for packaging.

In another aspect of the present disclosure, which may be combined with any other aspect listed herein unless specified otherwise, the scanner is configured to transmit the label patient information to at least one processor. Further, the router is configured to route the medication container to the output transport mechanism after receiving a matching signal indicative that the medication container is to be routed to the output transport mechanism when the processor matches the label patient information to the stored patient information in the fulfillment database, and route the medication container to the diverter transport mechanism after receiving a non-matching signal indicative that the medication container is to be routed to the diverter transport mechanism when the processor is unable to match the label patient information to patient information in the fulfillment database.

In another aspect of the present disclosure, which may be combined with any other aspect listed herein unless specified otherwise, the first end of the diverter transport mechanism includes the scanner configured to read the label on the medication container, and at least one container stop configured to prevent the medication container from being routed onto the output transport mechanism until the label patient information scanned by the scanner matches the patient information in the fulfillment database.

In another aspect of the present disclosure, which may be combined with any other aspect listed herein unless specified otherwise, the first end of the diverter transport mechanism includes the router configured to hold the medication container on the diverter transport mechanism for a defined time period route the medication container to a reject area when the defined time period has elapsed.

In another aspect of the present disclosure, which may be combined with any other aspect listed herein unless specified otherwise, the defined time period is five minutes, ten minutes, fifteen minutes, twenty minutes, or thirty minutes.

In another aspect of the present disclosure, which may be combined with any other aspect listed herein unless specified otherwise, the reject area includes at least one reject bin or at least one reject transport mechanism.

In another aspect of the present disclosure, which may be combined with any other aspect listed herein unless specified otherwise, the diverter transport mechanism in conjunction with the feed transport mechanism includes at least one conveyor track that is configured to have an oval-shape.

In another aspect of the present disclosure, which may be combined with any other aspect listed herein unless specified otherwise, fied otherwise, the infeed loop apparatus further comprises a second scanner located along the output transport mechanism, the second scanner configured to read the label on the medication container to obtain second label patient information, and at least one mover configured to move the medication container from the output transport mechanism to a dispensing mechanism for placement in a receptacle when the second label patient information from the second scanner matches the patient information in the fulfillment database.

In another aspect of the present disclosure, which may be combined with any other aspect listed herein unless specified otherwise, the second label patient information from the second scanner is transmitted to at least one processor that identifies which medication container is being dispensed into the receptacle.

In another aspect of the present disclosure, which may be combined with any other aspect listed herein unless specified otherwise, the processor is configured to determine whether the mover can move the medication container to the dispensing mechanism after confirming the second label patient information from the second scanner matches patient information indicative of medication documentation already placed into the receptacle.

In another aspect of the present disclosure, which may be combined with any other aspect listed herein unless specified otherwise, the dispensing mechanism includes a dispensing tube and a telescoping section configured to extend vertically toward the receptacle.

In another aspect of the present disclosure, which may be combined with any other aspect listed herein unless specified otherwise, the infeed loop apparatus further comprises a lateral movement section configured to move the dispensing tube laterally from the output transport mechanism to the receptacle, a pin configured to retain the medication container within the dispensing tube, and a pin actuator configured to remove the pin enabling the medication container to drop into the receptacle when the dispensing tube is laterally aligned with the receptacle and the telescoping section is extended.

In another aspect of the present disclosure, which may be combined with any other aspect listed herein unless specified otherwise, the feed transport mechanism includes at least one conveyor track.

In light of the disclosure herein and without limiting the disclosure in any way, in an aspect of the present disclosure, which may be combined with any other aspect listed herein unless specified otherwise, an infeed loop apparatus for a medication bagger system comprises at least one feed transport mechanism including an input end configured to receive at least one medication container and an exit end connected to a dispensing mechanism. The infeed loop apparatus further includes at least one diverter transport mechanism including a first end connected to the exit end of the feed transport mechanism, and a second end connected to the input end of the feed transport mechanism. Additionally, the infeed loop apparatus includes an output transport mechanism configured to dispense the medication container from the feed transport mechanism, a scanner located along a portion of the input end of the feed transport mechanism or the diverter transport mechanism, the scanner configured to read a label on the medication container to obtain label patient information, and a router connected to the exit end of the feed transport mechanism and the first end of the diverter transport mechanism, the router configured to selectively route the medication container to the output transport mechanism or the diverter transport mechanism, and a processor communicatively coupled to the scanner and the router. The processor is configured to receive the label patient information from the scanner, transmit a matching signal to the router to cause the router to route the medication container to the output transport mechanism when the label patient information matches patient information that is stored in the fulfillment database, and transmit a non-matching signal to the router to cause the router to route the medication container to the diverter transport mechanism when label patient information does not match the patient information stored in the fulfillment database.

In another aspect of the present disclosure, which may be combined with any other aspect listed herein unless specified otherwise, the label patient information and the patient information in the fulfillment database includes at least one of a patient identifier, a medication identifier, a medication quantity identifier, a dosage identifier, an urgency identifier, a weight value, a medication shape identifier, a medication manufacturer indicator, a dosage form indicator, a medication color indicator, a marking indicator, a Drug Enforcement Administration ("DEA") code, a prescription expiration date, a medication expiration date, pharmacist verification information, or a prescription status.

In another aspect of the present disclosure, which may be combined with any other aspect listed herein unless specified otherwise, the first end of the diverter transport mechanism includes the scanner configured to read the label on the medication container, and at least one container stop configured to prevent the medication container from being routed onto the output transport mechanism until the label patient information scanned by the scanner matches the patient information stored in the fulfillment database.

In another aspect of the present disclosure, which may be combined with any other aspect listed herein unless specified otherwise, the first end of the diverter transport mechanism includes the router, and the processor is further configured to cause the router to hold the medication container on the diverter transport mechanism for a defined time period, and cause the router to route the medication container to a reject area when the defined time period has elapsed.

In another aspect of the present disclosure, which may be combined with any other aspect listed herein unless specified otherwise, the defined time period is five minutes, ten minutes, fifteen minutes, twenty minutes, or thirty minutes.

In another aspect of the present disclosure, which may be combined with any other aspect listed herein unless specified otherwise, the reject area includes at least one reject bin or at least one reject transport mechanism.

In another aspect of the present disclosure, which may be combined with any other aspect listed herein unless specified otherwise, the diverter transport mechanism in conjunction with the feed transport mechanism includes at least one conveyor track that is configured to have an oval-shape.

In another aspect of the present disclosure, which may be combined with any other aspect listed herein unless specified otherwise, a medication documentation preparation apparatus for a medication bagger system comprises a tray configured to receive medication documentation, at least two rollers positioned next to each other to define a slit therebetween, and a gantry assembly configured to move between two positions. The gantry assembly includes a first arm, a second arm connected to the first arm, a pusher connected to an end of the second arm having a width that is less than the slit formed between the rollers, a first gantry gripper and a second gantry gripper that are each configured to engage the medication documentation, and a processor communicatively coupled to at least one motor for controlling the positioning of the gantry assembly, the movement of the first arm, the movement of the second arm, and at least one actuator for controlling engagement of the first gantry gripper and the second gantry gripper. The processor is configured to (a) cause the motor to move the gantry assembly to a position that is aligned with the tray, (b) cause the motor to move the first arm causing the pusher to push the medication documentation into the slit between the at least two rollers to fold the medication documentation, (c) cause the at least one actuator to engage the first and second gantry grippers with the folded medication documentation, (d) cause the motor to move the first arm away from the at least two rollers, (e) cause the motor to move the gantry assembly to a position that is aligned with a receptacle, (f) cause the motor to move the first arm to a dispense area, and (g) cause the motor to move the second arm to the dispense area, causing the medication documentation to be dispensed into the receptacle.

In another aspect of the present disclosure, which may be combined with any other aspect listed herein unless specified otherwise, the medication documentation preparation apparatus further comprises a bar code scanner configured to scan a bar code on at least one page of the medication documentation and the processor is further configured to compare patient information from the scanned bar code to patient information in a fulfillment database.

In another aspect of the present disclosure, which may be combined with any other aspect listed herein unless specified otherwise, the processor is further configured to cause the motor to move the first arm to cause the pusher to push the medication documentation into the slit between the at least two rollers to fold the medication documentation in half when the scanned patient information matches the patient information in the fulfillment database.

In another aspect of the present disclosure, which may be combined with any other aspect listed herein unless specified otherwise, the processor is further configured to skip (c) to (g) when the scanned patient information does not match the patient information in the fulfillment database.

In another aspect of the present disclosure, which may be combined with any other aspect listed herein unless specified otherwise, the processor is further configured to cause (i) the motor to move the first arm to an intermediate position, or (ii) the motor to move the first arm to a dispense position to push the medication documentation through the slit into the discard tray.

In another aspect of the present disclosure, which may be combined with any other aspect listed herein unless specified otherwise, the processor is further configured to generate an alert.

In another aspect of the present disclosure, which may be combined with any other aspect listed herein unless specified otherwise, the processor is further configured to skip (c) to (g) when the scanned patient information is indicative that a bar code cannot be read.

In another aspect of the present disclosure, which may be combined with any other aspect listed herein unless specified otherwise, the bar code scanner is configured to read a bar code located on a first page and a last page of the medication documentation.

In another aspect of the present disclosure, which may be combined with any other aspect listed herein unless specified otherwise, the medication documentation preparation apparatus further comprises a second bar code scanner configured to scan a bar code on the receptacle, wherein the processor is further configured to compare the scanned patient information from the scanned bar code on the medication documentation to patient information from the second bar code scanner.

In another aspect of the present disclosure, which may be combined with any other aspect listed herein unless specified otherwise, the processor is further configured to cause the motor to move the first arm to cause the pusher to push the medication documentation into the slit between the at least two rollers to fold the medication documentation in half when the scanned patient information matches the patient information in the fulfillment database.

In another aspect of the present disclosure, which may be combined with any other aspect listed herein unless specified otherwise, the processor is further configured to skip (c) to (g) when the scanned patient information does not match the patient information in the fulfillment database.

In another aspect of the present disclosure, which may be combined with any other aspect listed herein unless specified otherwise, the processor is further configured to cause (i) the motor to move the first arm to an intermediate position, or (ii) the motor to move the first arm to a dispense position to push the medication documentation through the slit into the discard tray.

In another aspect of the present disclosure, which may be combined with any other aspect listed herein unless specified otherwise, the processor is further configured to generate an alert.

In another aspect of the present disclosure, which may be combined with any other aspect listed herein unless specified otherwise, the processor is further configured to skip (c) to (g) when the scanned patient information is indicative that a bar code cannot be read.

In another aspect of the present disclosure, which may be combined with any other aspect listed herein unless specified otherwise, the tray includes at least two sidewalls and at least one stopper for aligning a center of the medication documentation over the at least two rollers.

In another aspect of the present disclosure, which may be combined with any other aspect listed herein unless specified otherwise, the medication documentation preparation apparatus further comprises a printer configured to print the medication documentation, and a transporter configured to move the medication documentation from the printer to the tray after receiving a signal from the processor.

In another aspect of the present disclosure, which may be combined with any other aspect listed herein unless specified otherwise, the transporter includes at least two paper rollers actuated by a roller motor.

In another aspect of the present disclosure, which may be combined with any other aspect listed herein unless specified otherwise, the medication documentation preparation apparatus further comprises a third gantry gripper and a fourth gantry gripper that are each configured to engage the medication documentation.

In another aspect of the present disclosure, which may be combined with any other aspect listed herein unless specified otherwise, the processor is further configured to cause a medication container to be dispensed into a receptacle after the medication documentation is dispensed.

In another aspect of the present disclosure, which may be combined with any other aspect listed herein unless specified otherwise, the tray includes a window located in a middle section of the tray and the at least two rollers are located within or beneath the window of the tray.

In another aspect of the present disclosure, which may be combined with any other aspect listed herein unless specified otherwise, a packaging apparatus for a medication bagger system comprises a main frame, a bag transport mechanism affixed to the main frame and configured to receive a plurality of bags, the printing station including at least a thermal transfer printer and a print roller, and the loading station including at least a first, second, and third articulable finger, at least a first and second bag gripper, an air knife, and a sealing mechanism. The bag transport mechanism cooperates with a motor used to transport at least one of the plurality of the bags to at least a printing station and a loading station. The first, second, and third articulable fingers are configured to engage a leading bag of the plurality of bags to enable medication documentation and at least one medication container to be placed therein. The first and second bag grippers are configured to engage the leading bag to prepare it for sealing and move away from the leading bag pulling the leading bag taut for a seal.

In another aspect of the present disclosure, which may be combined with any other aspect listed herein unless specified otherwise, the bags are a preformed length of bags attached to one another.

In another aspect of the present disclosure, which may be combined with any other aspect listed herein unless specified otherwise, the bags include a perforation on a back side of an inflation edge.

In another aspect of the present disclosure, which may be combined with any other aspect listed herein unless specified otherwise, the air knife is configured to direct air towards the inflation edge of the leading bag to open the leading bag.

In another aspect of the present disclosure, which may be combined with any other aspect listed herein unless specified otherwise, the bags are in a roll.

In another aspect of the present disclosure, which may be combined with any other aspect listed herein unless specified otherwise, the bag transport mechanism is a conveyor track.

In another aspect of the present disclosure, which may be combined with any other aspect listed herein unless specified otherwise, the bag transport mechanism is a plurality of rollers.

In another aspect of the present disclosure, which may be combined with any other aspect listed herein unless specified otherwise, the packaging apparatus further comprises a clutch positioned along the bag transport mechanism to control the rollers from spinning too fast.

In another aspect of the present disclosure, which may be combined with any other aspect listed herein unless specified otherwise, at least a portion of the printing station is affixed to a pivotable frame.

In another aspect of the present disclosure, which may be combined with any other aspect listed herein unless specified otherwise, the articulable fingers are moved by at least one pneumatic valve.

In another aspect of the present disclosure, which may be combined with any other aspect listed herein unless specified otherwise, the first and second bag grippers are configured to engage the leading bag after loading medication documentation and at least one medication container to translate relative one another to pull the leading bag taut.

In another aspect of the present disclosure, which may be combined with any other aspect listed herein unless specified otherwise, the loading station includes a static eliminating mechanism.

In another aspect of the present disclosure, which may be combined with any other aspect listed herein unless specified otherwise, the static eliminating mechanism is an ionizing bar.

In another aspect of the present disclosure, which may be combined with any other aspect listed herein unless specified otherwise, the sealing mechanism includes mating a heat seal bar with a silicone seal pad between a front side and a back side of the leading bag to form the seal on the leading bag.

In another aspect of the present disclosure, which may be combined with any other aspect listed herein unless specified otherwise, the packaging apparatus further comprises an opening sensor for detecting if the leading bag has been opened.

In another aspect of the present disclosure, which may be combined with any other aspect listed herein unless specified otherwise, a method for packaging medication comprises feeding a leading bag from a plurality of bags, via a motor and a bag transport mechanism, to a printing station; printing patient information onto a front side of the leading bag at the printing station by a thermal transfer printer and a print roller; transporting, via the bag transport mechanism, the leading bag to a loading station; opening the leading bag with an air knife configured to blow air directly into an inflation edge of the leading bag; engaging, via a first and second bag gripper configured to engage the leading bag and a first, second, and third articulable finger configured to pull the front side of the leading bag away from a back side of the leading bag; filling the leading bag with medication documentation and at least one medication container; moving the first and second bag grippers apart from one another to stretch the leading bag taut; and sealing the leading bag by a sealing mechanism.

In another aspect of the present disclosure, which may be combined with any other aspect listed herein unless specified otherwise, the bags are a preformed length of bags attached to one another.

In another aspect of the present disclosure, which may be combined with any other aspect listed herein unless specified otherwise, the bags include a perforation on the back side of the inflation edge.

In another aspect of the present disclosure, which may be combined with any other aspect listed herein unless specified otherwise, the packaging apparatus further comprises reverse indexing the motor while the sealing mechanism breaks the perforation on the leading bag.

In another aspect of the present disclosure, which may be combined with any other aspect listed herein unless specified otherwise, the packaging apparatus further comprises mating a heat seal bar with a silicone seal pad between the front side and back side of the leading bag to form a seal on the leading bag.

In another aspect of the present disclosure, any of the structure, functionality, and alternatives disclosed in connection with any one or more of FIGS. 1A to 15 may be combined with any other structure, functionality, and alternatives disclosed in connection with any other one or more of FIGS. 1A to 15.

In light of the present disclosure and the above aspects, it is therefore an advantage of the present disclosure to provide a single modular machine that automatically packages single medication containers and corresponding documentation into a bag or other receptacle.

It is another advantage of the present disclosure to use multiple scanners to ensure the correct medication container is placed with the correct medication documentation in a bag or other receptacle without manual operator verification.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. In addition, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1A:
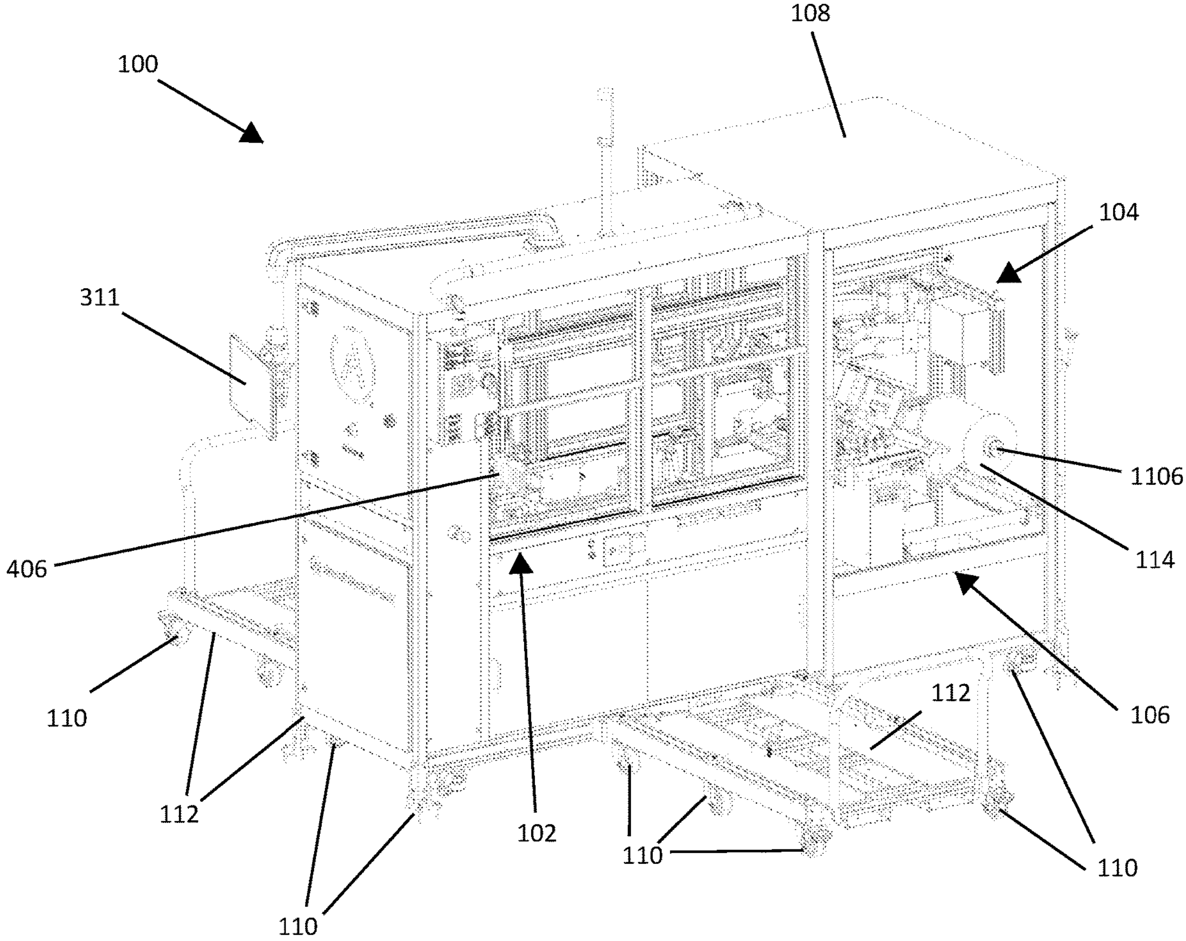
FIG. 1A shows an isometric front view of the medication bagger system, according to an example embodiment of the present disclosure.

Methods, systems, and apparatus are disclosed herein for automatically bagging containers and corresponding documentation. The automated bagging of medication containers enables thousands of medication prescriptions to be efficiently fulfilled each day. The methods, systems, and apparatus are configured to use one or more scanners to read a label on a medication container and/or printed medical documentation to ensure the mediation and documentation is bagged for a given patient, thereby reducing or eliminating potential errors.

Reference is made herein to medication documentation. As disclosed herein, medication documentation is generated by a pharmacy based on a medication order provided by a clinician (commonly referred to as a prescription). The medication documentation includes patient information and a medication order. The medication order designates a particular patient for receiving a specific dosage of a medication. In other words, the medication documentation refers to a single medication fill event for a particular patient. The medication documentation also includes a unique identifier for tracking the medication container, such as a bar code. The bar code may be any type of identifier known in the industry including one-dimensional bar codes, two-dimensional bar codes, stock keeping unit ("SKU"), radio frequency identification ("RFID"), or quick response codes ("QR codes"). In the described embodiments, the unique identifier is a bar code 11, but it will be appreciated that the use of a bar code is purely exemplary.

Patient information includes information regarding a particular patient and required medication needs. This may include, but is not limited to, information including a patient identifier, a medication identifier, a medication quantity identifier, a dosage identifier, an urgency identifier, a weight value, a medication shape identifier, a medication manufacturer indicator, a dosage form indicator, a medication color indicator, a marking indicator, a Drug Enforcement Administration ("DEA") code, a prescription expiration date, a medication expiration date, pharmacist verification information, a prescription status, medication directions, and/or the number of pages of medication documentation when printed. This patient information is stored in a fulfillment database that can be accessed and cross-referenced by a processor and/or a controller of a medication bagger system.

Reference is also made herein to medication containers. A medication container refers to a medication bottle, vial carrier, pill pack, blister card, package, or other container for housing and moving medication. The medication held within the medication container may include pills, tablets, or other solid pharmaceutical drug dosage that is consumed by a patient. A medication may also include a compounded pharmaceutical that is prepared from two or more substances.

A medication container usually includes a lid to ensure the medication stored within is secured and not able to be contaminated by exposure to outside elements. The medication container also includes a label with medication information and/or patient information. The label also includes a unique identifier for tracking the medication container, such as a bar code. In some embodiments, the medication container may include a separate identifier to enable tracking of the medication container itself within a pharmacy automation system and/or a medication bagger system.

While the example methods, apparatus, and systems are disclosed herein as operating with medication documentation and medication containers, it should be appreciated that the methods, apparatus, and systems may be operable with other articles. For example, the methods, apparatus, and systems may provide for the routing of packages in a facility, products to be packaged in a facility, and/or components to be assembled into a product along an assembly line. The methods, apparatus, and systems are likewise applicable to a wide variety of products including, but not limited to, manufactured goods, perishable goods, food products, medical products, and other commercial products. It will be appreciated that the methods, apparatus, and systems may be used in other contexts as known by a person having ordinary skill in the art.

The example methods, apparatus, and systems disclosed below are more efficient than known packaging systems. The apparatuses disclosed herein, including a medication bagger system 100 and accompanying medication documentation preparation apparatus 102, infeed loop apparatus 104, and packaging apparatus 106, reduce the number of procedural steps compared to the known bagging and packaging methods and may do so at faster speeds.

Figure 1B:
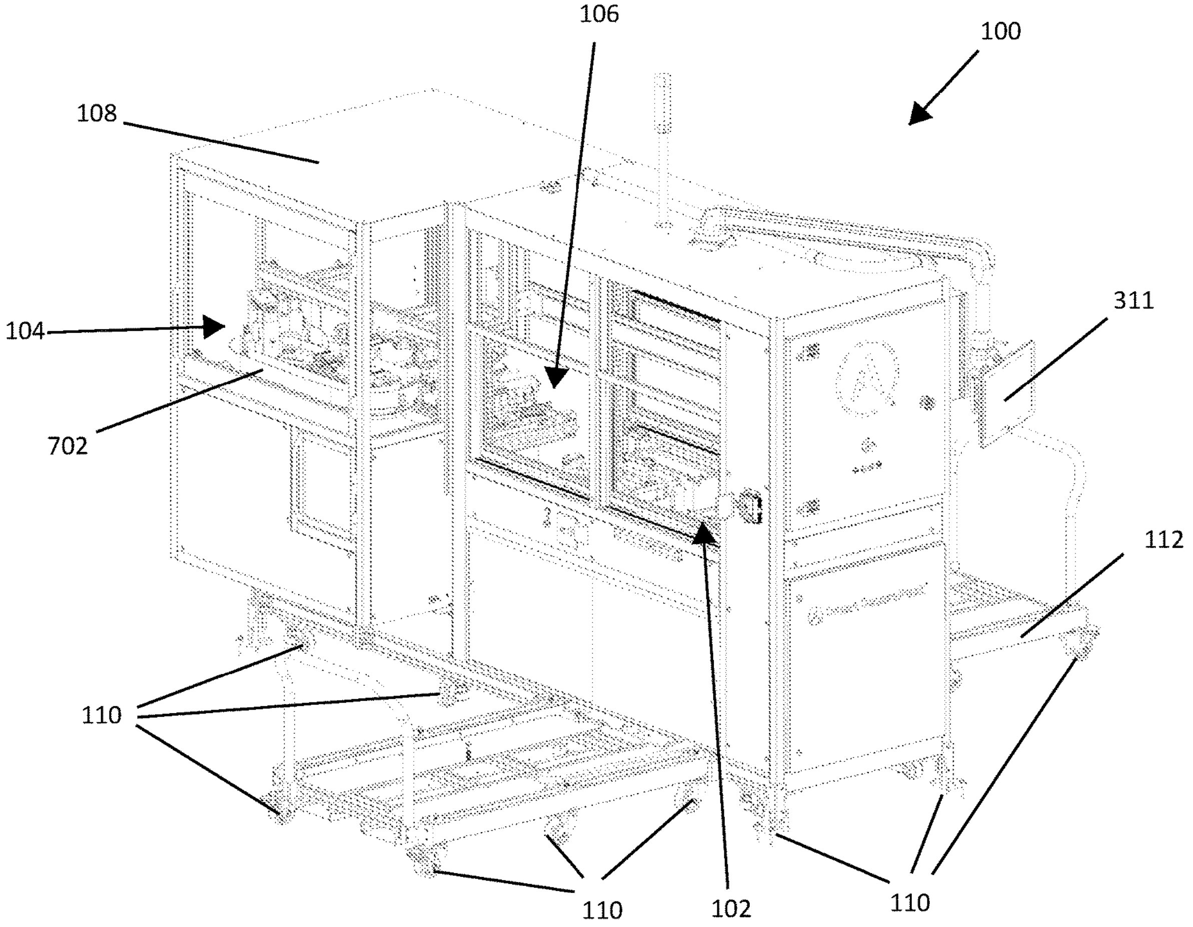
FIG. 1B shows an isometric back view of the medication bagger system, according to an example embodiment of the present disclosure.

Referring now to FIGS. 1A and 1B, the medication bagger system 100 includes a medication documentation preparation apparatus 102, an infeed loop apparatus 104, and a packaging apparatus 106. Each of the medication documentation preparation apparatus 102, the infeed loop apparatus 104, and the packaging apparatus 106 may operate contemporaneously. It should be appreciated that the medication bagger system 100 has been simplified to make the description of the present disclosure easier, and that the medication bagger system 100, if implemented, would have additional structure and functionality.

Depending on the embodiment, the medication documentation preparation apparatus 102, the infeed loop apparatus 104, the packaging apparatus 106, and other components of the medication bagger system 100 may all be physically connected by framing, may be partially connected by framing, or may be physically separated. In the illustrated embodiment, a main frame 108 connects the medication documentation preparation apparatus 102, the infeed loop apparatus 104, and the packaging apparatus 106. The main frame 108 may consist of metal framing. In some embodiments, the main frame 108 can be on wheels 110 such that the medication bagger system 100 can be easily moved and re-arranged. Additionally, the main frame 108 can integrate drawer slides 112 so that the medication bagger system 100 can be adjusted and moved to reach internal systems such as the medication documentation preparation apparatus 102, the infeed loop apparatus 104, or the packaging apparatus 106.

Figure 2A:
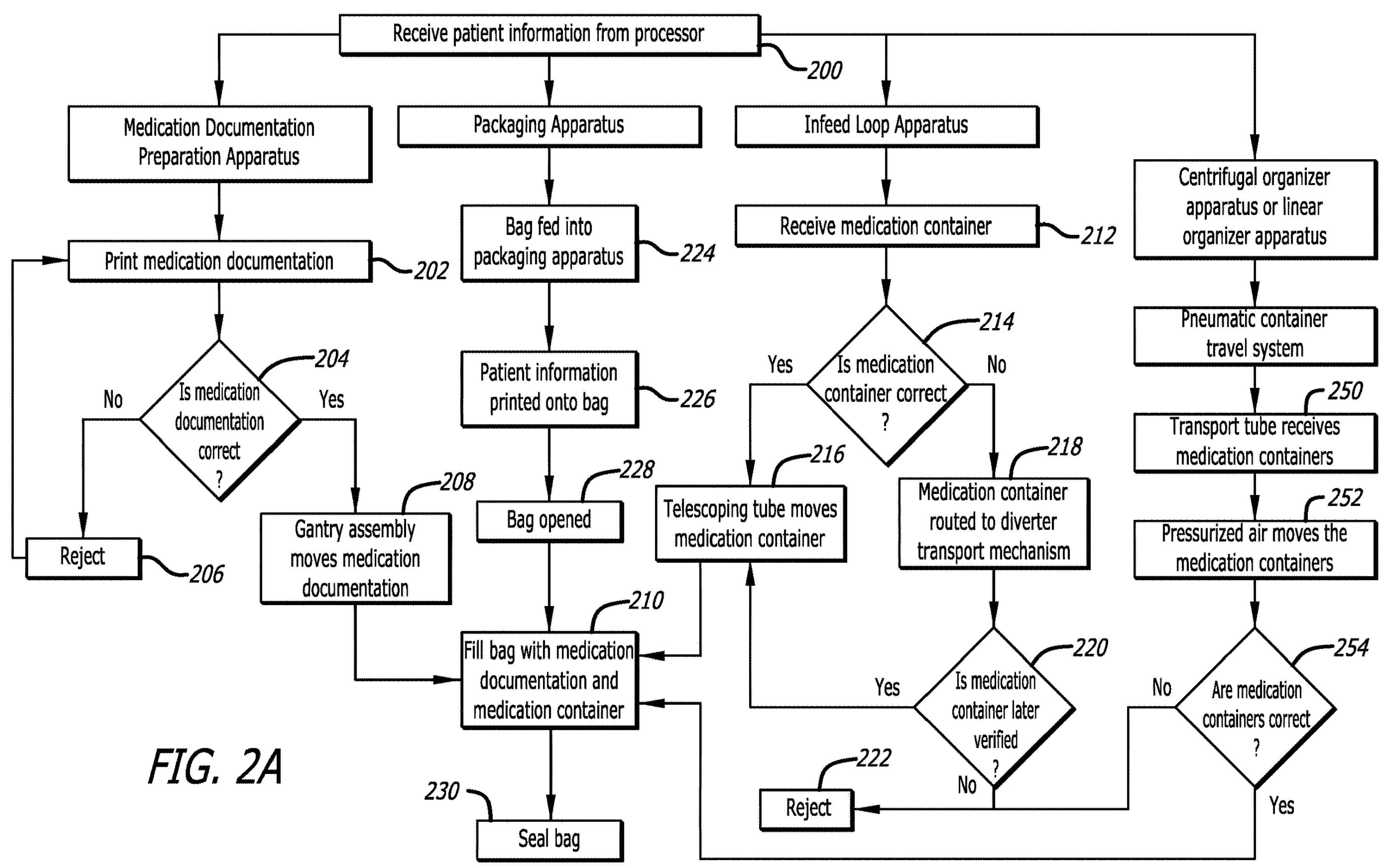
FIG. 2A is a diagram of the medication bagger system process, according to an example embodiment of the present disclosure.

The medication bagger system 100 allows receptacles, such as bags 114, to be filled and packaged with medication documentation 10 and medication containers 20 that are matched to patient information. While described in more detail below, this process is shown at a high level in FIG. 2A and tracks the operations of the medication documentation preparation apparatus 102, the infeed loop apparatus 104, and the packaging apparatus 106. Patient information is received by the system (block 200) and is routed to the medication documentation preparation apparatus 102, the infeed loop apparatus 104, and the packaging apparatus 106. The processes associated with each of the medication documentation preparation apparatus 102, the infeed loop apparatus 104, and the packaging apparatus 106 are individually shown in FIGS. 2B-2D, respectively. In the medication documentation preparation apparatus process illustrated in FIG. 2B, medication documentation 10 is printed (block 202). Once printed, the medication documentation 20 is verified (block 204). If it is incorrect, it is rejected (block 206) and optionally may be reprinted. If it is correct, it is moved by a gantry assembly (block 208) for placement into a bag (block 210). Contemporaneously, the infeed loop apparatus process occurs, as illustrated in FIG. 2C, when the medication container 20 is received (block 212) by the infeed loop apparatus. The medication container 20 is also verified (block 214). Verification is described further below. If the medication container 20 is correct, it is moved by a telescoping tube (block 216) to be deposited into a bag (block 210). If it is incorrect, the medication container 20 is routed to a different area, known as a diverter transport mechanism (block 218). The medication container 20 may be independently verified by a pharmacist or operator and after a predetermined time period, it is again verified (block 220). If it again cannot be verified, it is rejected (block 222). If it can now be verified, the medication container 20 is moved by the telescoping tube (block 216) to be deposited into the bag (block 210). To prepare the bag for loading, the bag is fed into a packaging apparatus (block 224) and the packaging apparatus process of FIG. 2D begins. Patient information is printed onto the bag (block 226) and the bag is opened (block 228). The bag is filled with the medication documentation 10 from the medication documentation preparation apparatus and medication container 20 from the infeed loop apparatus (block 210). Once the bag is filled (block 210), the bag is sealed (block 230).

The processes illustrated in FIG. 2A-2D may occur concurrently, in tandem, or in sequence with other steps as described further below. For instance, the operations of the medication documentation preparation apparatus may occur simultaneously with the operations of the infeed loop apparatus, or the operations of each apparatus may occur at different times. Additionally, processes may depend on one another to initiate. In some embodiments, the medication documentation may be printed upon signal that the telescoping tube has begun to move medication containers 20 in the infeed loop apparatus to the packaging apparatus. In other embodiments, the packaging process of FIG. 2D may not begin until the medication documentation preparation apparatus process of FIG. 2B and the infeed loop apparatus process of FIG. 2C have been completed. It will be appreciated that many variations of the order and process of the methods illustrated in FIG. 2A-2D may be apparent to a person having ordinary skill in the art.

Figure 3:
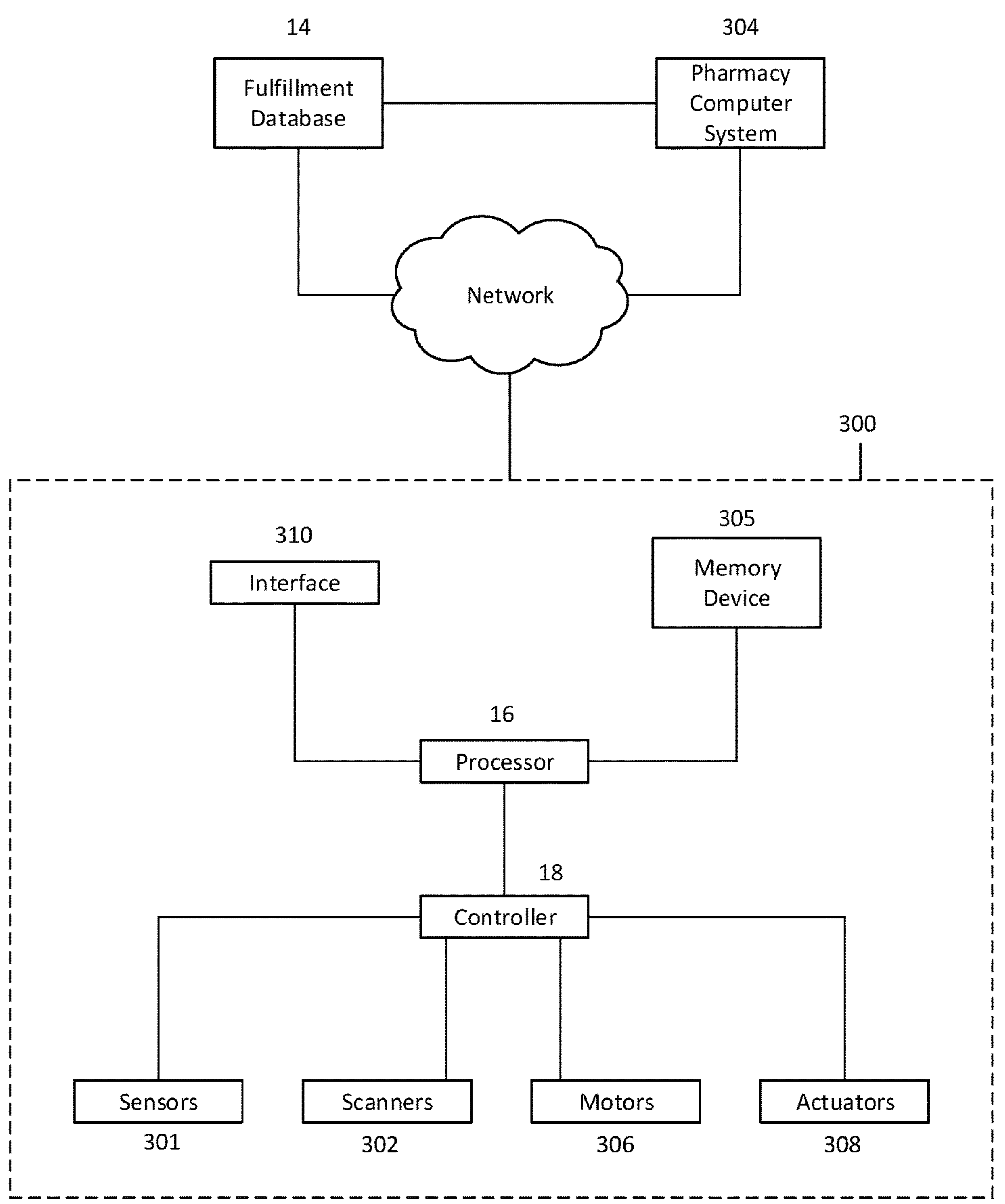
FIG. 3 is a diagram of the communication system in the medication bagger system, according to an example embodiment of the present disclosure.

FIG. 3 illustrates an application server 300 configured to control the medication bagger system 100. The application server 300 may be connected to the medication documentation preparation apparatus 102, the infeed loop apparatus 104, and the packaging apparatus 106 via a local area network ("LAN"), a wireless LAN, a serial connection such as RS 232 or RS 485, a controller area network ("CAN") connection, an Ethernet connection, Open Platform Communications ("OPC"), IO-Links, a hardwire connection, or other various connections as known by a person having ordinary skill in the art. In some embodiments, the application server 300 may communicate using a Fieldbus or Hart communication protocol.

The example application server 300, as illustrated in FIG. 3, includes a memory device 305, an interface 310, a processor 16, and a centralized logic controller 18, though other application servers may further include a workstations, a laptop computer, a distributed computing system, etc. The application server 300 is communicatively coupled to a pharmacy computer system 304 and/or a fulfillment database 14.

The application server 300 may include a memory device 305 that stores machine-readable instructions, which when executed, cause the application server 300 to perform the operations disclosed herein. Additionally, the application server 300 is communicatively coupled to the memory device 305, which may include any random access memory ("RAM"), read only memory ("ROM"), flash memory, magnetic or optical disks, optical memory, or other storage media. The memory device 305 is configured to store instructions for routing the medication documentation 10 and medication containers 20.

In some embodiments, the memory device 305 may store movement instructions regarding the routing of medication documentation 10 and medication containers 20 in a database. In these embodiments, the application server 300 uses the interface 310 to communicate with the medication documentation preparation apparatus 102, the infeed loop apparatus 104, the packaging apparatus 106, and the database in the memory device 305.

In the illustrated embodiment, the application server 300 may be communicatively coupled to the pharmacy computer system 304 via a LAN connection, a serial connection such as RS 232 or RS 485, a CAN connection, an Ethernet connection, OPC, IO-Links, a hardwire connection, or other various connections as known by a person having ordinary skill in the art. In some embodiments, the application server 300 may communicate using a Fieldbus or Hart communication protocol.

The pharmacy computer system 304 is configured to transmit patient information from the fulfillment database 14 to the processor 16 of the application server 300 via the interface 310. Alternatively, the application server 300 receives the patient information directly from the fulfillment database 14. The pharmacy computer system 304 may also provide a queue order that indicates which medication orders are being routed to the medication bagger system 100.

The processor 16 of the application server 300 may include a user interface 311 that provides options for an operator or pharmacist to directly override decisions and movement instructions by the processor 16. The user interface 311 can be a screen that displays parameters such as patient information or information related to the efficiency and efficacy of various components of the medication bagger system 100.

The application server 300 is configured to process the patient information in a defined workflow to ensure a prescription is fulfilled using the medication bagger system 100 via the processor 16. Processing includes the processor 16 determining how the medication order is to be filled and whether both the medication documentation 10 and the medication container 20 are correct at various stages throughout the fulfillment process, as described further below. The processor 16 may be connected to the medication bagger system 100 components through the controller 18. These components such as scanners 302 can be communicatively coupled via a local area network ("LAN"), a wireless LAN, a serial connection such as RS 232 or RS 485, a controller area network ("CAN") connection, an Ethernet connection, Open Platform Communications ("OPC"), IO-Links, a hardwire connection, or other various connections known by a person having ordinary skill in the art. In some embodiments, the processor 16 may communicate using a Fieldbus or Hart communication protocol.

The processor 16 is also communicatively coupled with at least one logic controller 18. The processor 16 can transmit movement instructions to the controller 18, which converts the movement instructions into signals or messages for motors 306 and/or actuators 308 of the medication bagger system 100. The controller 18 includes an interface for receiving movement instructions and receiving updates to movement instructions from the processor 16. The signals and/or messages cause the motors 306 and/or the actuators 308 to move in a specified manner. The motors 306 and actuators 308 receive the signals and/or messages from the controller 18, which are used to directly control the motors 306 and actuators 308. The motors 306 and/or actuators 308 can include pneumatic slides, transport mechanisms such as conveyors, gantries, and/or routers. The controller 18 can include at least one programmable logic controller ("PLC"). In instances where the controller 18 includes PLCs, the controller interface may include a PLC table interface.

In order to properly ensure that a patient receives the appropriate order, the medication container 20 and medication documentation 10 are tracked by sensors 301 and scanners 302. Sensors 301 may be used to track the weight of medication documentation 10 or medication containers 20, verify that medication documentation 10 or medication containers 20 are contained within the medication bagger system 100, as well as determine whether the medication documentation 10 or medication containers 20 are at various stages of the process. The bar codes 11 that are printed or otherwise encoded on medication documentation 10 and each medication container 20 are periodically scanned by scanners 302 throughout the routing, bagging, and packaging processes to verify a match. Scanners 302 read the bar code 11 and transmit the read label (patient) information to the application server 300. It should be appreciated that the scanners 302 identified in the application are exemplary and other scanners 302 may be added or omitted in other embodiments of the medication bagger system 100. Additionally, the plurality of scanners 302 within the medication bagger system 100 need not be configured in the same manner.

As shown in FIG. 3, the sensors 301 and scanners 302 communicate with the controller 18 and processor 16 to determine movement instructions: the appropriate route for the medication documentation 10 and medication container 20. These movement instructions are updated as the application server 300 uses the present location of the medication documentation 10 or medication container 20 to determine one or more next stations that the medication documentation 10 or medication container 20 will pass in the medication bagger system 100.

Medication Documentation Preparation Apparatus Embodiment

Figure 4A:
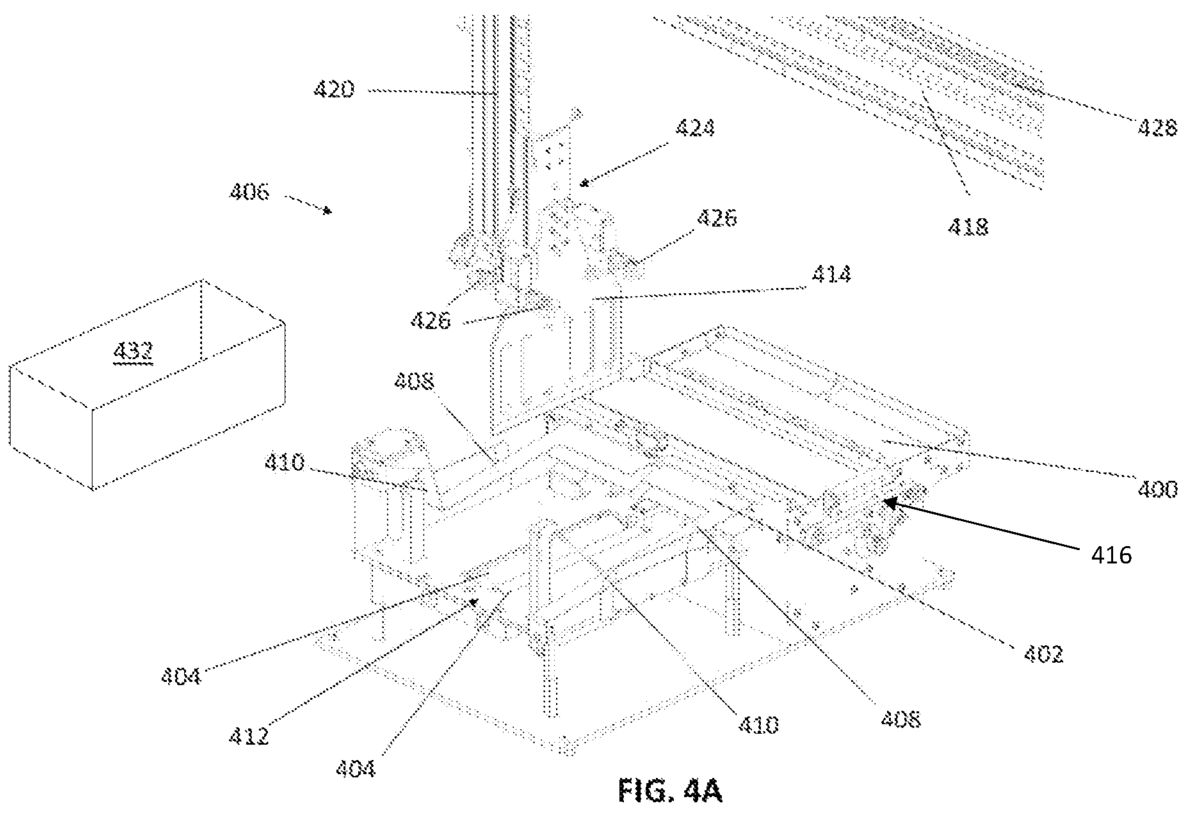
FIG. 4A shows the medication documentation preparation apparatus prior to medication documentation being fed into the apparatus, according to an example embodiment of the present disclosure.
Figure 4B:
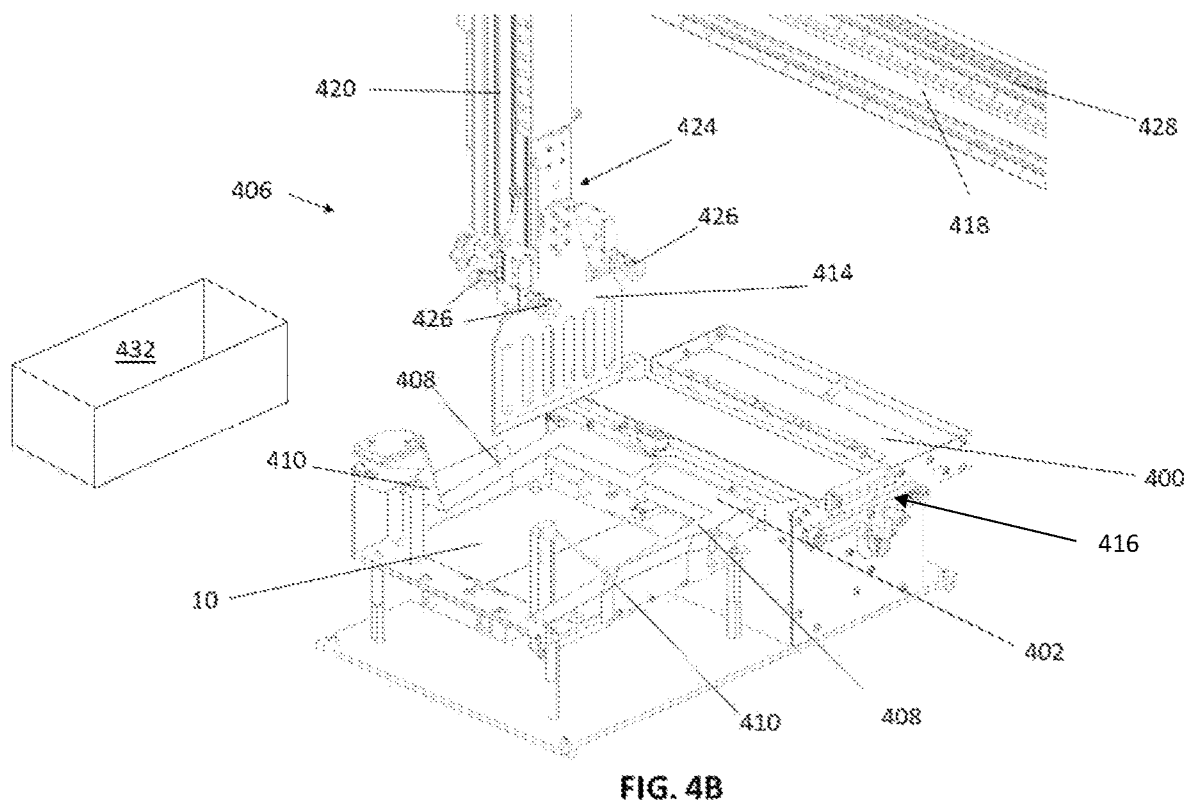
FIG. 4B shows medication documentation fed into the medication documentation preparation apparatus, according to an example embodiment of the present disclosure.
Figure 4C:
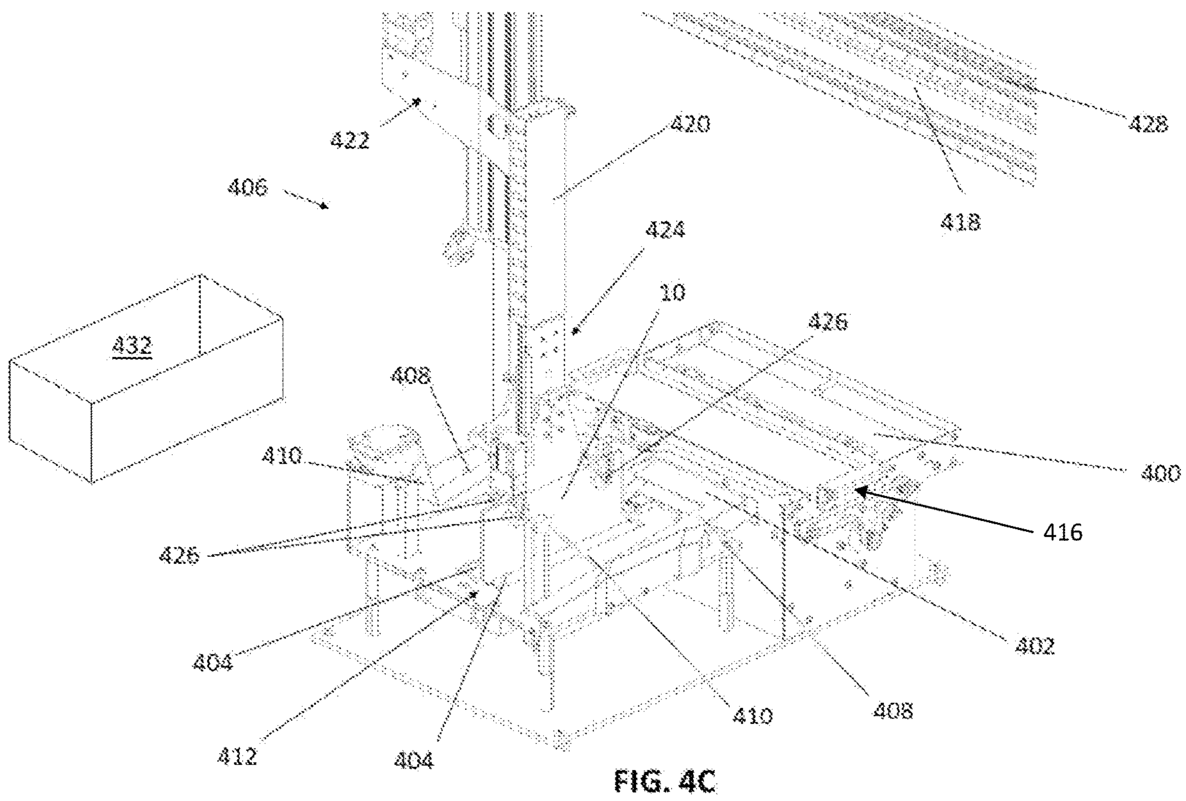
FIG. 4C shows the medication documentation being folded within the medication documentation preparation apparatus, according to an example embodiment of the present disclosure.
Figure 4D:
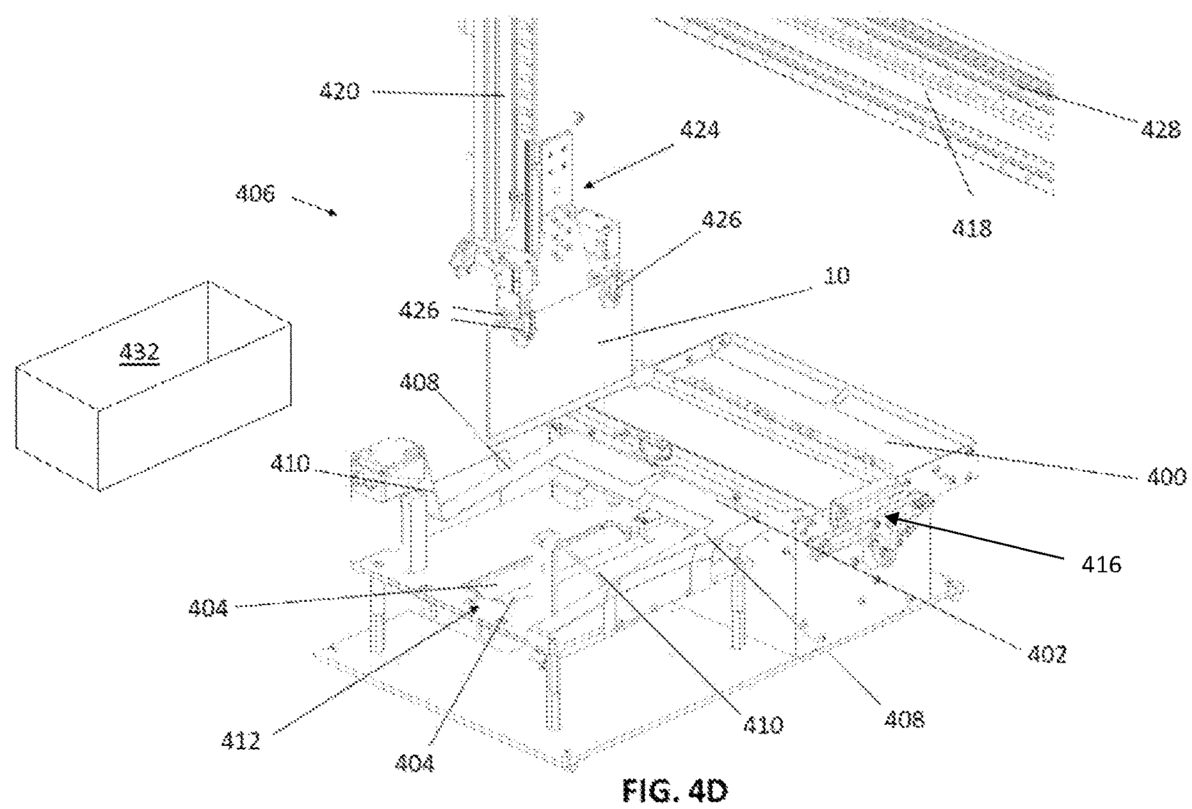
FIG. 4D shows the medication documentation being lifted by the gantry assembly in the medication documentation preparation apparatus, according to an example embodiment of the present disclosure.
Figure 5:
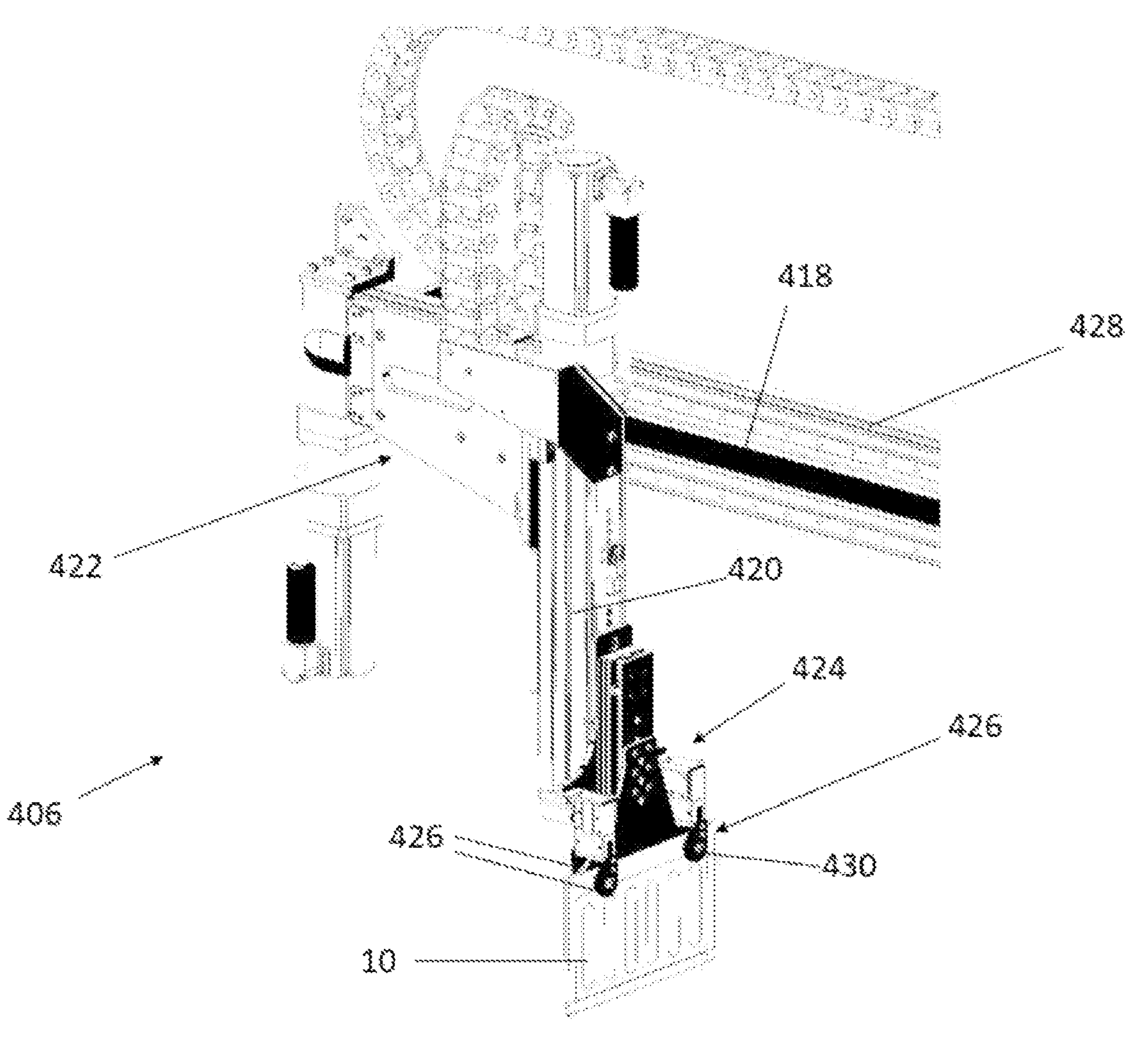
FIG. 5 shows an isometric view of the gantry assembly, according to an example embodiment of the present disclosure.

FIGS. 4A-6 illustrate the medication documentation preparation apparatus 102, which includes at least one printer 400, a tray 402, at least two rollers 404, and a gantry assembly 406, according to an example embodiment of the present disclosure. The medication documentation preparation apparatus 102 also includes a moveable gantry assembly 406. The gantry assembly 406 comprises a first arm 418, a second arm 420 connected to the first arm 418, a pusher 414 connected to an end 424 of the second arm 420, and gantry grippers 426. A close-up view of the gantry assembly 406 is shown in FIG. 5.

The first arm 418 includes a track 428 for the second arm 420 to move along. In the illustrated embodiments, the first arm 418 is approximately parallel relative to the ground and the second arm 420 is approximately perpendicular to the ground. The second arm 420 is configured to move laterally along the length of the first arm 418 by an actuator 308 programmed to receive movement instructions from the controller 18. The second arm 420 is configured to also move vertically by an actuator 308 programmed to receive movement instructions from the controller 18. Affixed at the end 424 of the second arm 420 is the pusher 414. The pusher 414 is a thin component devised to fold medication documentation 10 around it. The pusher 414 may be any material sufficiently strong enough to push paper between the rollers 404. The pusher 414 has a width that is less than the slit 412 formed between the rollers 404 so that the pusher 414 can fit between the slit 412.

Also connected to the end 424 of the second arm 420 are the gantry grippers 426. Each gantry gripper 426 includes at least two arms 430 designed to engage the medication documentation 10. The arms 430 are symmetric to one another. Upon receipt of movement instructions from the processor 16, the controller 18 initiates at least one actuator 308 to extend the gantry grippers 426 to pinch the medication documentation 10. When brought together, the arms 430 move toward one another to squeeze the medication documentation 10. Then, the gantry grippers 426 are configured to hold the medication documentation 10 as the gantry assembly 406 moves. When the gantry grippers 426 are not engaged with the medication documentation 10, the gantry grippers 426 rest at a position perpendicular to the second arm 420. This position allows the pusher 414 to fully fold the medication documentation 10 without the gantry grippers 426 hampering the fold. In some embodiments, a third and fourth gantry gripper 426 are also configured to engage the medication documentation 10. FIGS. 4A-4D show the medication documentation preparation apparatus 102 in various states throughout the medication documentation preparation process. The medication documentation preparation process begins with printing the medication documentation 10. The printer 400 receives the patient information for the medication documentation 10 from the controller 18 and/or the processor 16. The controller 18 triggers a scanner 302 to scan a bar code 11 on a label 22 of a medication container 20 that is located in infeed loop apparatus 104. The bar code 11 is used to poll the fulfillment database 14. The resulting matching information is then relayed back to the controller 18 for printing the medication documentation 10.

In some embodiments, a scanner 302 at the infeed loop apparatus 104 scans a bar code 11 of a next medication container to be dispensed. The scanner 302 may be located at an entrance to the infeed loop apparatus 104 and/or at an exit of the infeed loop apparatus 104. Label patient information read from the scanner 302 is used by the processor 16 to query the fulfillment database 14 to confirm the patient information matches patient information in the fulfillment database 14. After a match is made between the patient information, the processor 16 is configured to use at least some of the patient information to print the medication documentation 10 using the printer 400.

The application server 300 controls the medication documentation preparation apparatus 102. As discussed above, the application server 300 transmits movement instructions to the controller 18, which implement the movement instructions. The controller 18 is communicatively coupled to motor(s) 306 for controlling the positioning of the gantry assembly 406, the movement of the first arm 418, the movement of the second arm 420, and the actuators 308.

The controller 18, in some embodiments, uses Simple Network Management Protocol ("SNMP") to determine when the printer 400 is available to print the patient information to create medication documentation 10. The controller 18 also employs modular printing systems to transmit and receive print commands. This modular printing system can be customized to appropriately control the medication documentation preparation apparatus 102. The custom modular printing system may be built using pre-existing modular printing systems such as Linux Common UNIX Printing System ("Linux CUPS").

There are a variety of printer states that can be returned to the controller 18, which may include information that the printer 400 is ready to print, the printer 400 has open doors that must be manually closed, the printer 400 is out of paper, or that the printer 400 is not ready to print for any other reason.

When the controller 18 determines that the printer 400 is ready to print the medication documentation 10 (block 202 in FIG. 2B), the controller 18 polls the printer 400 to determine if there is a queue of medication documentation 10 to be printed. If the queue is empty, the controller 18 triggers the medication documentation 10 to print. If the queue is not empty, the controller 18 waits until the queue empties before relaying movement instructions to the printer 400. The controller 18 directs the printing queue and can override the already existing queue when the controller 18 determines it to be necessary.

After the medication documentation 10 is printed, the medication documentation 10 exits the printer 400, and it is transferred to the tray 402 by the transporter 416. As shown in FIG. 4A, the tray 402 includes at least two sidewalls 408 and at least one stopper 410 for aligning a center of the medication documentation 10 over at least two rollers 404 upon receipt from the printer 400. The rollers 404 are stationary when the medication documentation 10 arrives in the tray 402 and may be kept stationary by brakes or other stoppage mechanisms as known to a person having ordinary skill in the art. The rollers 404 may be any material sturdy enough that allows the medication documentation 10 to roll. However, in a preferred embodiment, the rollers 404 are a metal, such as a stainless steel, which allows the rollers 404 to freely spin, but not be so light that the rollers 404 slip while assisting in the folding of the medication documentation 10. The rollers 404 have a pre-defined distance, e.g., a slit 412, between them. The slit 412 is a distance into which medication documentation 10 can fold. Because medication documentation 10 can be a range of pages of paper, the slit 412 is large enough to accommodate thicker medication documentation 10. When the medication documentation 10 is folded by the pusher 414 of the gantry assembly 406 as described below, the medication documentation 10 folds into the slit 412.

Upon the printer 400 printing the medication documentation 10, the medication documentation 10 is moved from the printer 400 to a tray 402 by a transporter 416 as shown in FIG. 4B. In illustrated embodiments, the transporter 416 may be a ramp to the tray 402 and guides on the sidewalls 408 of the tray 402 that the medication documentation 10 follows upon the printer 400 ejecting the medication documentation 10 directly onto the tray 402. In other embodiments, the transporter 416 includes paper rollers actuated by a motor 306. In yet other embodiments, the transporter 416 may be a conveyor track, a belt conveyor system, plurality of rollers, or a dial machine indexer. If necessary, the transporter 416 is activated by the controller 18 when the printer 400 begins printing the medication documentation 10.

In some embodiments, the transporter 416 leads the medication documentation to the tray which may include a window located in a middle section of the tray. In some embodiments, the window may be transparent. In other embodiments, the rollers may be located within or beneath the window of the tray.

Figure 2B:
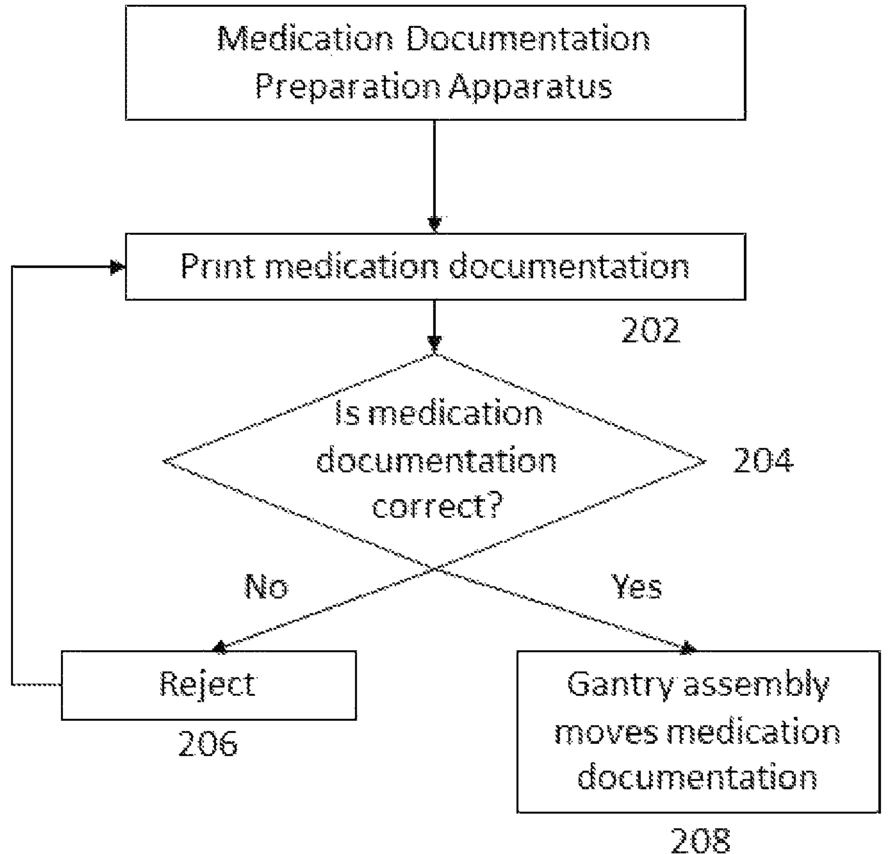
FIG. 2B is a diagram of the medication documentation preparation apparatus process, according to an example embodiment of the present disclosure.
Figure 2C:
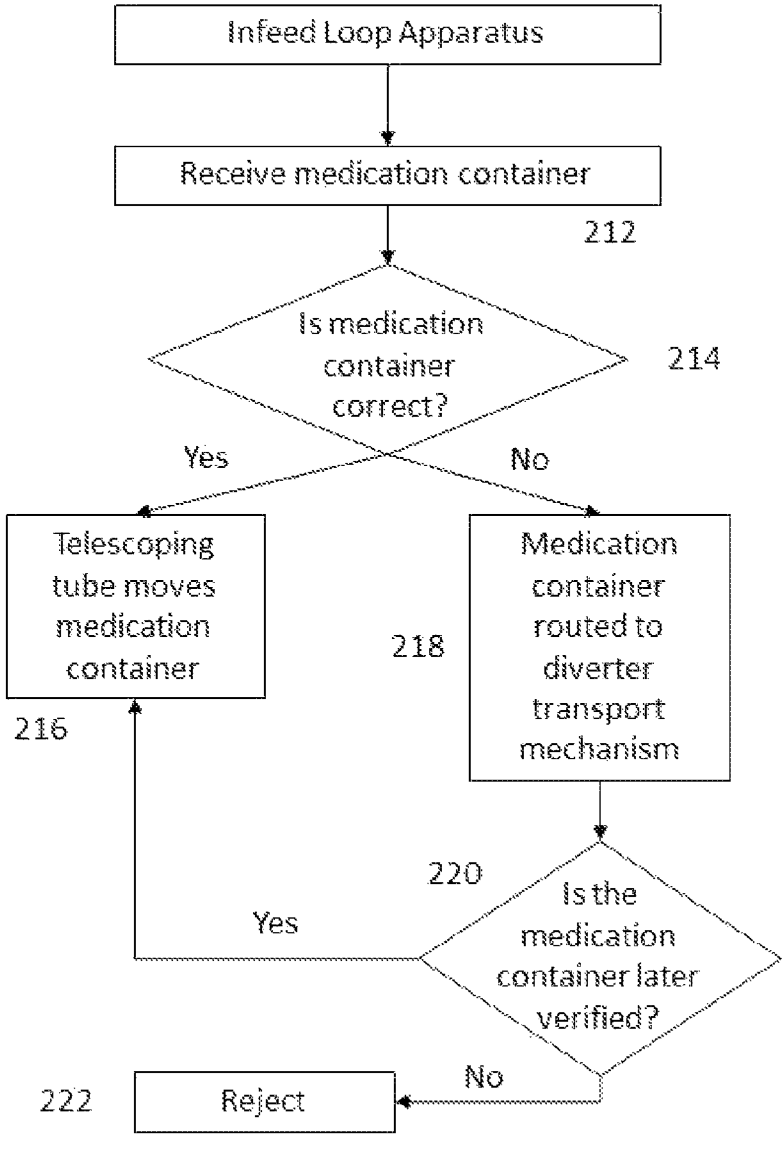
FIG. 2C is a diagram of the infeed loop apparatus process, according to an example embodiment of the present disclosure.
Figure 2D:
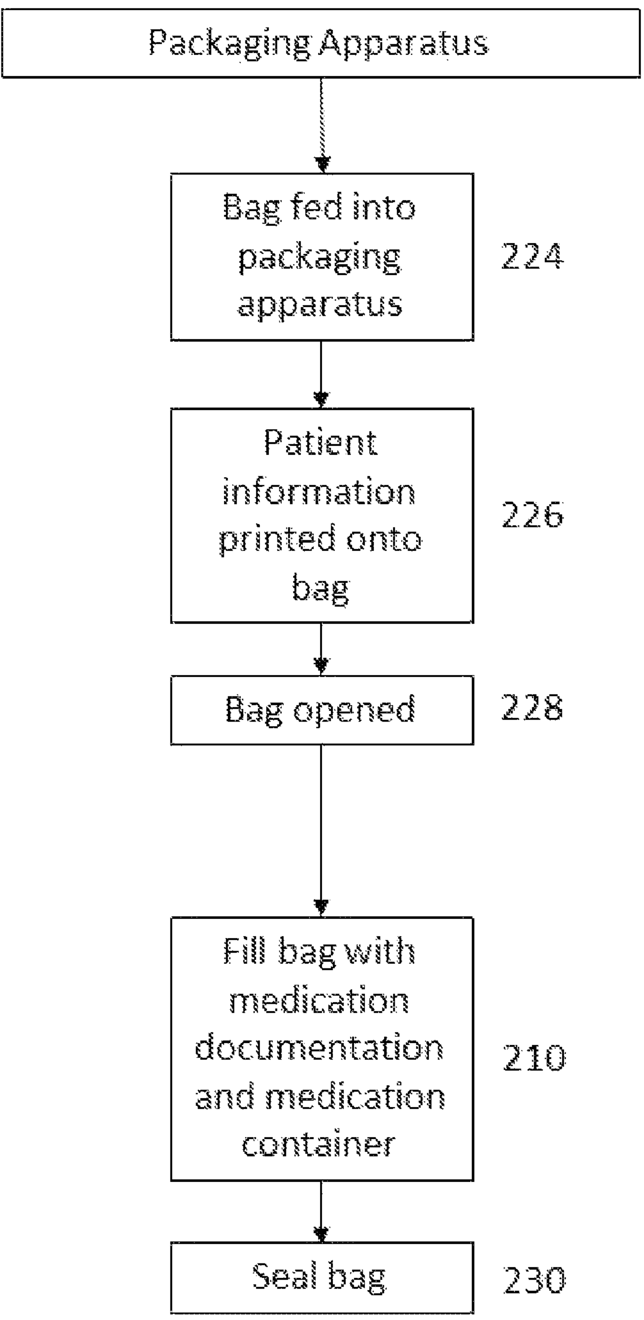
FIG. 2D is a diagram of the packaging apparatus process, according to an example embodiment of the present disclosure.

As shown in FIG. 2B, the medication documentation 10 is verified for accuracy (block 204). Once printed, a sensor 301 measures a number of pages in the medication documentation 10. This may occur at the tray 402 or the transporter 416. The page count must match the page count stored in the fulfillment database 14. When the page count does not match, the medication documentation 10 is rejected for patient safety and security (block 206). In some instances, the processor 16 is configured to receive the information indicative of the page count from the sensor 301. The processor 16 uses a page count in the patient information stored at the fulfillment database 14 to determine at least one page is missing. In some embodiments, the processor 16 causes the gantry assembly 406 via the controller 18 to pick up and move (or push) the incorrect medication documentation 10 to a documentation reject area 432 when a page count is not correct. When the medication documentation 10 is rejected, the controller 18 is configured to instruct the printer 400 to re-print the medication documentation 10.

In addition, the scanner 302 scans the first and last page of the medication documentation 10 to check for a match in the fulfillment database 14. The scanner 302 communicates with the processor 16 to verify the match. When bar codes 11 on either the first or the last page of the medication documentation 10 do not match the patient information in the fulfillment database 14 or cannot be read or scanned, the medication documentation 10 is rejected.

When medication documentation 10 is rejected, the processor 16 determines the proper course of action based on the printer queue and other system parameters. The processor 16 chooses between three courses of action. The medication documentation preparation apparatus 102 continues to operate during a rejection.

A first course of action when the medication documentation 102 is rejected is for the processor 16 to transmit movement instructions to the controller 18 to configure the motor 306 to move the first arm 418 of the gantry assembly 406 to an intermediate position. Once the gantry assembly 406 has been moved, the scanner 302 retries scanning the bar codes 11 to verify that at least one of the bar codes 11 does not match the patient information in the fulfillment database 14.

A second course of action when the medication documentation 10 is rejected is for the processor 16 to transmit movement instructions to the controller 18 to cause the motor 306 to move the first arm 418 of the gantry assembly 406 so that the pusher 414 can push the medication documentation 10 into the slit 412 between the rollers 404 to fold the medication documentation 10 in half. This movement is shown in FIG. 4C. The pusher 414 moves approximately four inches downward in this step, so as to avoid fully pushing the medication documentation 10 through the slit 412 between the rollers 404. When the pusher 414 is moved between the rollers 404, the rollers 404 spin to assist folding the medication documentation 10. After the pusher 414 is in position creating a physical crease on the medication documentation 10, the processor 16 causes the actuator 308 to engage the gantry grippers 426 with the folded medication documentation 10. The gantry grippers 426 pinch the medication documentation 10 and hold the medication documentation 10 as the first arm 418 moves the gantry assembly 406 back upwards away from the rollers 404. The processor 16 then transmits movement instructions to the controller 18 to configure the motor 306 to move the first arm 418 of the gantry assembly 406 to an intermediate position located above a medication documentation reject area 432. The gantry grippers 426 then release the medication documentation 10 into the medication documentation reject area 432 which may be any area configured to hold the rejected medication documentation, such as a discard tray. Then, the gantry assembly 406 returns to a position located above the tray 402 to reset. The tray 402 is now clear for a re-print of the medication documentation 10 and is ready to receive a new copy of the medication documentation 10 from the transporter 416 as illustrated by blocks 206 and 202 in FIG. 2B.

A third course of action when the medication documentation 10 is rejected is for the processor 16 to generate an alert. The alert notifies an operator to manually review the medication documentation 10. The operator may have a handheld scanner 302 to read the bar codes 11 on the medication documentation 10. When the operator determines that the medication documentation 10 does not match the patient information in the fulfillment database 14, the operator can manually remove the medication documentation 10, deposit it into the medication documentation reject area 432, and use the user interface 311 to notify the processor 16 that tray 402 is empty. When the operator determines that the medication documentation 10 matches the patient information in the fulfillment database 14, the operator can manually operate the user interface 311 to notify the processor 16 that the medication documentation 10 is correct.

When both (A) the page count of the medication documentation 10 match the page count listed in the fulfillment database 14, and (B) the bar codes 11 match with the patient information in the fulfillment database 14, the gantry assembly 406 follows a set of movement instructions from the processor 16 (via the controller 18) to prepare and package the medication documentation 10. First, the processor 16 causes the motor 306 to move the gantry assembly 406 to a position aligned with the tray 402 where the pusher 414 is directly above the slit 412. Then, the processor 16 causes the motor 306 to move the first arm 418 of the gantry assembly 406, which causes the pusher 414 to push the medication documentation 10 into the slit 412 between the rollers 404 to fold the medication documentation 10 in half. This is shown in FIG. 4C. The pusher 414 moves approximately four inches downward in this step, so as to avoid fully pushing the medication documentation 10 through the slit 412 between the rollers 404. When the pusher 414 is moved between the rollers 404, the rollers 404 spin to assist the medication documentation 10 in its fold.

After the pusher 414 is in position creating a physical crease on the medication documentation 10, the processor 16 causes the actuator 308 to engage the gantry grippers 426 with the folded medication documentation 10. The gantry grippers 426 pinch the medication documentation 10 and hold the medication documentation 10 as the second arm 420 moves the gantry assembly 406 back upwards away from the rollers 404. A sensor 301 angled towards the rollers 404 verifies that all medication documentation 10 has been lifted by the gantry grippers 426. If not all medication documentation 10 has been lifted, the second arm 420 will retry to grip the medication documentation 10 or the medication documentation 10 will be rejected. The lifted medication documentation 10 can be seen in FIG. 4D.

Figure 6:
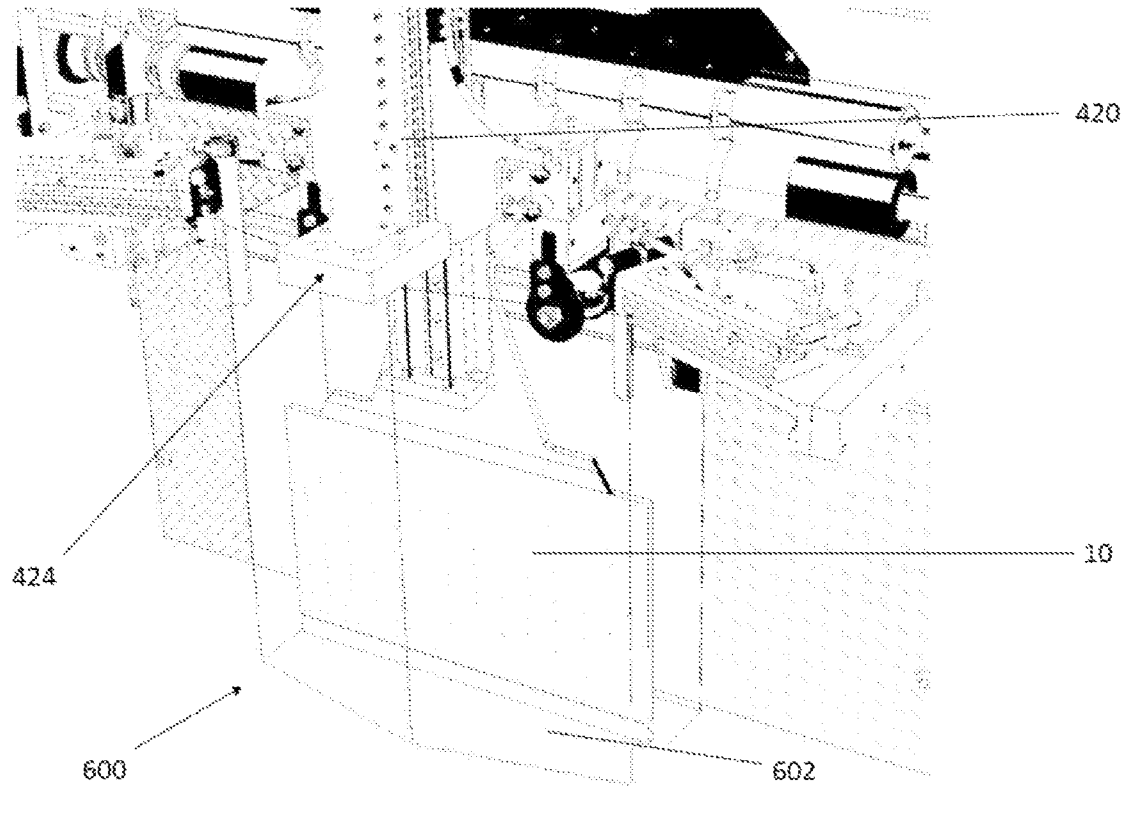
FIG. 6 shows an isometric view of the dispense area, according to an example embodiment of the present disclosure.
Figure 7A:
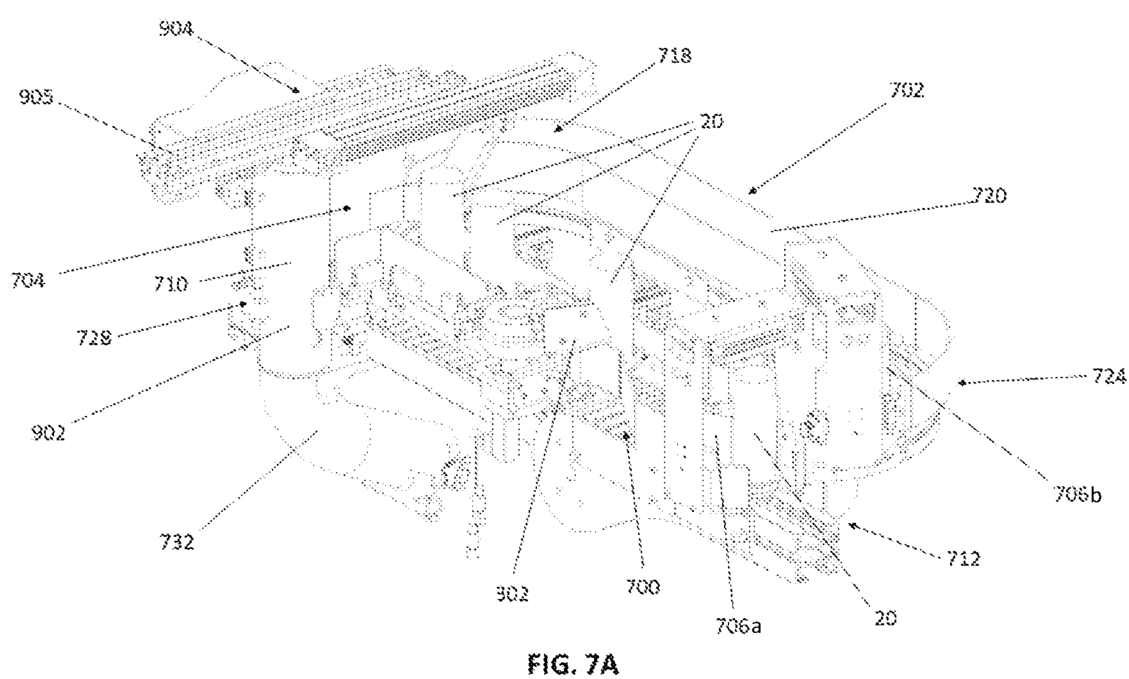
FIG. 7A shows a front view of the infeed loop apparatus, according to an example embodiment of the present disclosure.
Figure 7B:
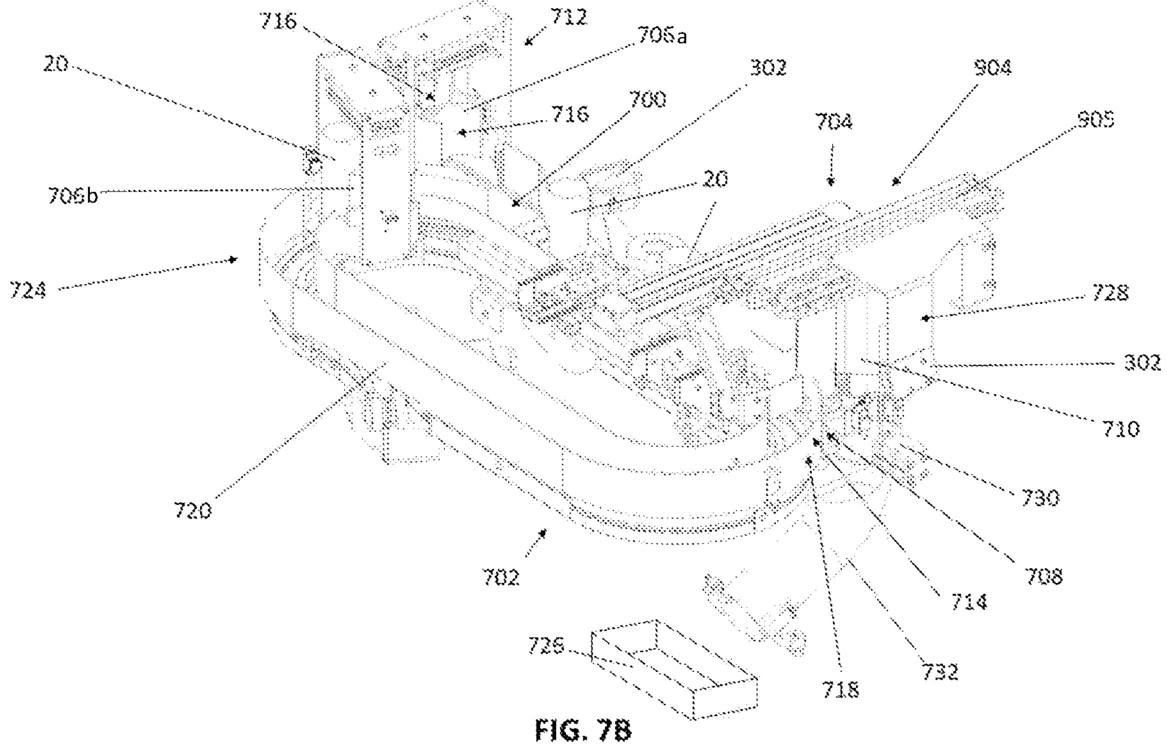
FIG. 7B shows a back view of the infeed loop apparatus, according to an example embodiment of the present disclosure.
Figure 8A:
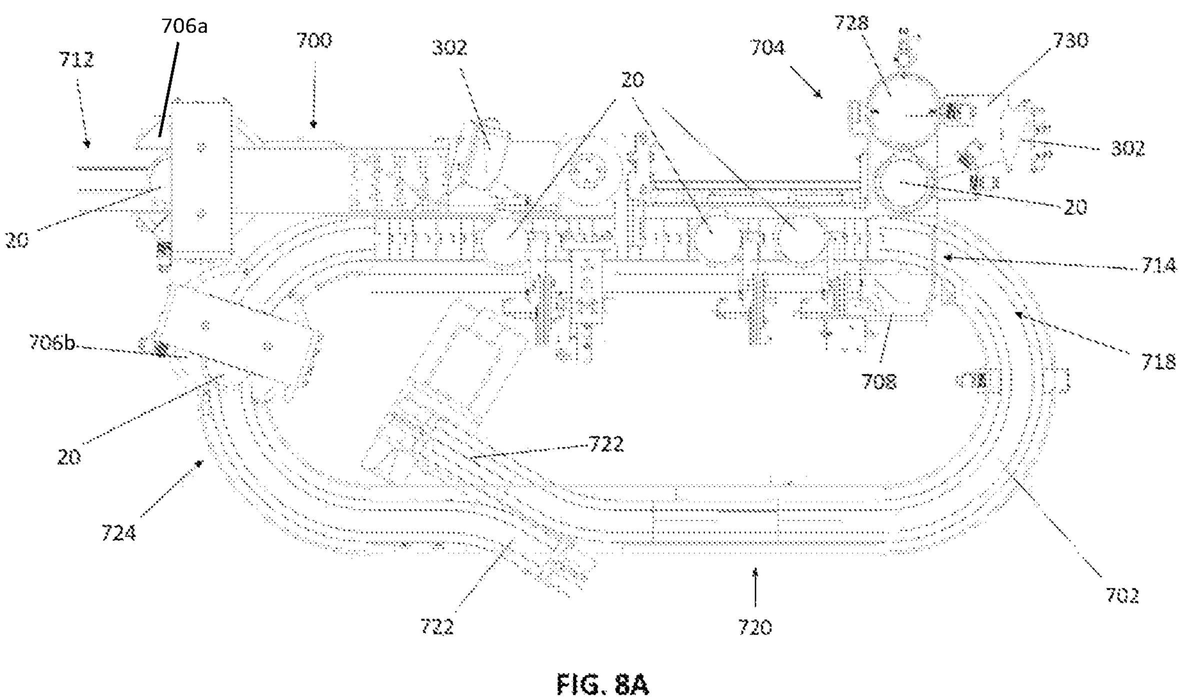
FIG. 8A shows a top view of the infeed loop apparatus with a medication container prior to being pushed into the dispensing tube, according to an example embodiment of the present disclosure.
Figure 8B:
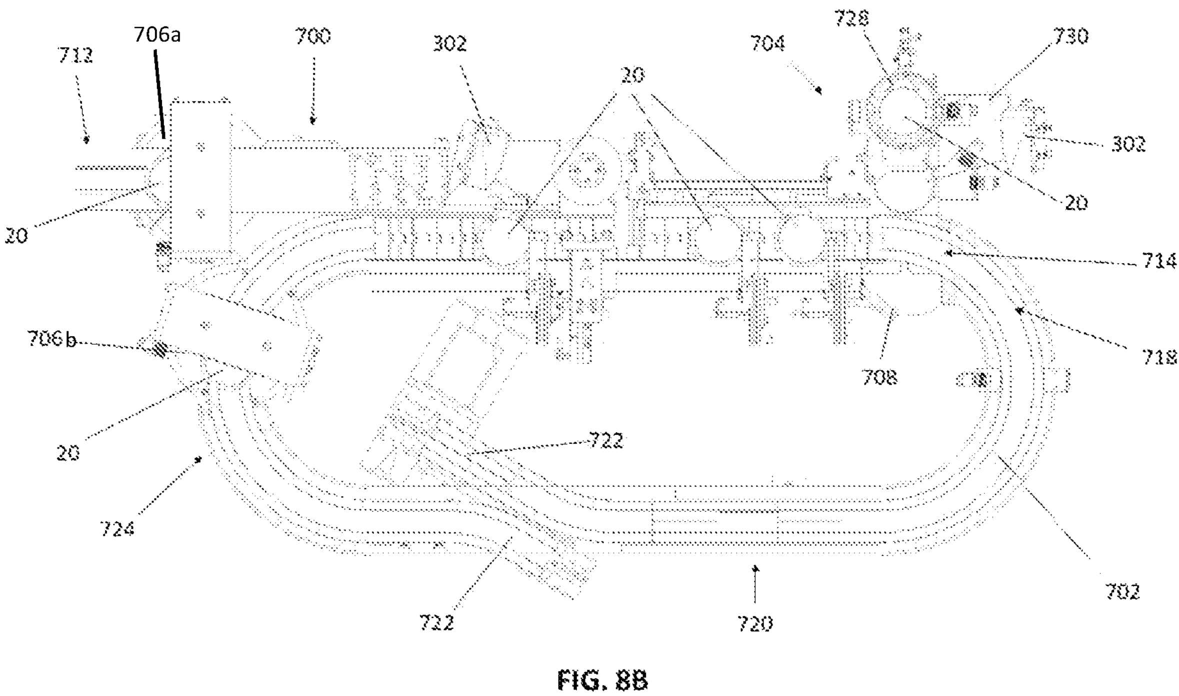
FIG. 8B shows a top view of the infeed loop apparatus with a medication container in the dispensing tube, according to an example embodiment of the present disclosure.

At this point, a scanner 302 located in a dispense area 600 (shown in FIG. 6) scans a bar code 11 located in the dispense area 600 shown in FIG. 6. The dispense area 600 may include a receptacle 602 (e.g., a container) into which the medication documentation 10 can be inserted. The receptacle 602 may be a bag 114 as described in more detail below. When the dispense area 600 includes a receptacle 602, the receptacle 602 has a bar code 11 adhered to its surface. This bar code 11 is scanned by the scanner 302 to verify that the receptacle 602 matches the patient information of the medication documentation 10. In some embodiments, the receptacle 602 omits a bar code such that scanning of the receptacle is omitted.

When the patient information on the receptacle 602 in the dispense area 600 is confirmed to match, the processor 16 causes the motor 306 to move the gantry assembly 406 to a dispense position that is directly above the dispense area 600. The processor 16 then causes the motor 306 to move the second arm 420 of the gantry assembly 406 downward toward the dispense area 600. As the second arm 420 moves, the actuator 308 connected to the pusher 414, pushes the medication documentation 10 down and out of the gantry grippers 426, causing the medication documentation 10 to be pushed thoroughly into any receptacle 602 in the dispense area 600 without losing the fold shape provided by the gantry assembly 406, as shown in FIG. 6. At this point, the medication documentation 10 is folded in the dispense area 600 and removed from the gantry assembly 406. The gantry grippers 426 return to a position perpendicular to the second arm 420 of the gantry assembly 406.

The processor 16 then instructs the motor 306 to return the gantry assembly 406 to its position over the tray 402 to allow the next medication documentation 10 to begin the medication documentation preparation process 102.

Infeed Loop Apparatus Embodiment

FIGS. 7A-9C illustrate the infeed loop apparatus 104, according to an example embodiment of the present disclosure. The infeed loop apparatus 104 includes a feed transport mechanism 700, a diverter transport mechanism 702, an output transport mechanism 704, routers 706*a*, 706*b*, a mover 708, and a dispensing tube 710.

The feed transport mechanism 700 is configured to receive pre-labeled medication containers 20 and can receive more than one medication container 20 contemporaneously (block 212 in FIG. 2C). The medication containers 20 may be fed into the feed transport mechanism 700 in a variety of manners, including but not limited to, manually feeding, conveying by conveyor belt or dial machine indexer, or rolling the medication containers 20 down ramps.

In the illustrated embodiment, the feed transport mechanism 700 is a conveyor track. In other embodiments, the feed transport mechanism 700 may be a belt conveyor system, a plurality of rollers, a configuration of ramps and sidewalls, or a dial machine indexer. The feed transport mechanism 700 includes an input end 712, which is configured to receive at least one medication container 20. The feed transport mechanism 700 is connected to the diverter transport mechanism 702, and output transport mechanism 704 at an exit end 714. The feed transport mechanism 700 is configured to move the medication containers 20 towards the exit end 714.

At the input end 712 of the feed transport mechanism 700, a router 706*a* briefly holds the medication container 20 so that a scanner 302 can scan the bar code 11 located on the label 22 of the medication container 20. The patient information associated with the bar code 11 is transmitted to the processor 16, which compares the label patient information to patient information in the fulfillment database 14. The router 706*a*, as described below, moves to allow the medication container 20 to continue along the feed transport mechanism 700.

In illustrated embodiments, each router 706*a*, 706*b* includes two concave openings 716 intended to receive a medication container 20. In other embodiments, the router 706*a*, 706*b* can be any device intended to hold and subsequently route the medication container 20 based on movement instructions received by the controller 18. The routers 706*a*, 706*b* are configured to selectively route the medication container 20 based on patient information indicative as to whether the medication container 20 is ready for packaging. In some embodiments, the routers 706*a*, 706*b* can rest on a turntable, or routing table, which rotates based on movement instructions received by the controller 18. This can be a 180-degree rotation to allow the medication container 20 to pass by the router 706*a*, 706*b*. In other embodiments, the router 706 itself can physically rotate by brackets affixed to either side of the router 706, which are operatively controlled by the controller 18. If the router 706 rotates by itself, it pushes the selected medication container 20 to the appropriate location. In yet other embodiments, the router 706 may be a pusher designed to push the medication container 20 to the appropriate location. It should be appreciated that the routers 706*a*, 706*b* identified in the application are exemplary and other routers 706*a*, 706*b* may be added or omitted in other embodiments of the medication bagger system 100. Additionally, if multiple routers 706*a*, 706*b* exist on the same infeed loop apparatus 104, they need not be configured in the same manner.

At the exit end 714 of the feed transport mechanism 700, the medication container 20, the medication container label 22 is scanned by a scanner 302 to read the bar code 11 on the medication container 20. The patient information associated with the bar code 11 is transmitted by the scanner 302 to the processor 16. The processor 16 is configured to identify if the label patient information contained within the bar code 11 on the medication container 20 matches the patient information in the fulfillment database 14. One of the primary data points verified in the fulfillment database 14 is whether a pharmacist has verified the prescription associated with the patient information.

If the processor 16 identifies that the patient information contained within the bar code 11 on the medication container 20 does not match the patient information in the fulfillment database 14 (or the prescription cannot otherwise be fulfilled), the processor 16 transmits movement instructions causing the controller 18 to not move an actuator 308 which directs the medication container 20 to the diverter transport mechanism 702 (block 218).

The first end 718 of the diverter transport mechanism 702 is also connected to the output transport mechanism 704. If the processor 16 identifies that the label patient information contained within the bar code 11 on the medication container 20 matches the patient information in the fulfillment database 14, the processor 16 transmits movement instructions causing the controller to push the actuator 308 to direct the medication container 20 to the output transport mechanism 704 (block 216).

This is a convergence point of the first end 718 of the diverter transport mechanism 702, the exit end 714 of the feed transport mechanism 700, and the output transport mechanism 704. The first end 718 of the diverter transport mechanism 702 further includes another bar code scanner 302. If the processor 16 identifies that the patient information contained within the bar code 11 on the medication container 20 does not match the patient information in the fulfillment database 14, the processor 16 transmits movement instructions to the controller 18 and the controller 18 does not cause the actuator 308 to move, thus allowing the medication container 20 to continue to the diverter transport mechanism 702. There are two common reasons for the label patient information on the medication container 20 to not match the patient information in the fulfillment database 14. First, a pharmacist may not have manually verified and approved the medication order. Second, the order may have been cancelled. It should be appreciated that these two scenarios identified in the application are merely exemplary and other scenarios may arise where the label patient information does not match the patient information in the fulfillment database 14.

The diverter transport mechanism 702 includes a conveyor track that is configured to have a semi-oval shape with a straight edge 720. In some embodiments, the straight edge 720 of the diverter transport mechanism 702 may include diversions 722 such as those shown in FIGS. 8A and 8B. These diversions 722 may be configured to route medication containers 20 in more complex manners than that described in this application. In other embodiments, the diverter transport mechanism 702 may be a belt conveyor system, a plurality of rollers, a configuration of ramps and sidewalls, or a dial machine indexer. The diverter transport mechanism 702 includes the first end 718 which is connected to the exit end 714 of the feed transport mechanism 700. The diverter transport mechanism 702 also includes a second end 724 connected to the feed transport mechanism 700 near the input end 712 of the feed transport mechanism 700.

If a medication container 20 is in the diverter transport mechanism 702 because a pharmacist has not approved the medication order, an alert is sent from the processor 16 to the pharmacy computer system 304. The pharmacy computer system 304 then notifies a pharmacist to verify the prescription associated with the patient information assigned to the medication container 20, beginning a secondary medication verification as illustrated in block 220 of FIG. 2C. At the second end 724 of the diverter transport mechanism 702, the medication container 20 is held for a defined time period. As an example, the defined time period may be five minutes, ten minutes, fifteen minutes, twenty minutes, or thirty minutes.

During the predetermined time period, the pharmacist can virtually verify the patient information associated with the medication container 20 and can transmit movement instructions to the processor 16. If the pharmacist determines that the medication container 20 and corresponding patient information is correct and should continue from the diverter transport mechanism 702 to the output transport mechanism 704, the pharmacist can virtually notify the application server 300 that the medication container 20 is to be moved from the diverter transport mechanism 702 through use of the pharmacy computer system 304. The medication container 20 is then routed back onto the feed transport mechanism 700 by a router 706*b*, where the medication container 20 begins the verification process again. Any medication containers 20 in front of the verified mediation container 20 are cycled through the feed transport mechanism 700 back to the diverter transport mechanism 702 since those containers are still not verified but need to be moved to enable the verified mediation container 20 to proceed to bagging.

If the pharmacist does not manually override the alert within the specified time period, the controller 18 is configured to divert the medication container 20 to a medication container reject area 726 at the end of the defined time period (block 206). In illustrated embodiments, the medication container reject area 726 is an area located beneath the output transport mechanism 704. When the defined time period ends, a router 706*b* at the second end 724 of the diverter transport mechanism 702 directs the medication container 20 to move back onto the feed transport mechanism 700. Once the medication container 20 reaches the first end 718 of the diverter transport mechanism 702, the mover 708 loads the medication container 20 into the dispensing tube 710 located within the output transport mechanism 704. The mover 708 moves along one axis and is configured to direct the medication container 20. The mover 708 contains a concave opening such that when a medication container 20 engages with the mover 708, the mover 708 is able to direct the medication container 20 along its path of travel.

The dispensing tube 710, which normally contains a pin and a pin actuator 730 to act as a floor for the medication container 20 as described below, receives instructions from the controller 18 for the pin actuator 730 to retract the pin away from the dispensing tube 710 so that the medication container 20 falls directly through the dispensing tube 710 and into the medication container reject area 726. In some embodiments, there may be a reject transport mechanism 732 which directs the medication container 20 to a medication container reject area 726 located away from the output transport mechanism 704. In the illustrated embodiments, the reject transport mechanism 732 is a chute.

When the medication container 20 is in the diverter transport mechanism 702 because the medication order has been cancelled, after being routed to the diverter transport mechanism 702, the processor 16 and/or the controller 18 is configured to divert the medication container 20 to the medication container reject area 726 at the end of the defined time period. As an example, the defined time period may be five minutes, ten minutes, fifteen minutes, twenty minutes, or thirty minutes. The defined time period may differ between medication containers 20 that were diverted due to pharmacist error versus medication containers 20 that were diverted due to order cancellation.

If, when the medication container 20 is at the feed transport mechanism 700, the processor 16 identifies that the label patient information contained within the bar code 11 on the medication container 20 matches the patient information in the fulfillment database 14, the processor 16 transmits movement instructions to the controller 18, which causes the mover 708 to direct the medication container 20 to the output transport mechanism 704. In the illustrated embodiment, the mover 708 pushes the medication container 20 off of the feed transport mechanism 700 and onto the output transport mechanism 704. Prior to the processor's 16 movement instructions, the mover 708 remains drawn back so as not to block the feed transport mechanism 700 from the diverter transport mechanism 702.

The output transport mechanism 704 includes a dispensing mechanism 728 to dispense the medication container 20. In the illustrated embodiments, the dispensing mechanism 728 is the dispensing tube 710. In other embodiments, the dispensing mechanism 728 may be a gantry, a claw, a conveyor, or other mover.

The dispensing tube 710 includes an inner tube 900 and an outer tube 902. The inner tube 900 is affixed to a lateral movement section 904 that comprises a frame 905. The outer tube 902 surrounds the inner tube 900 as a sleeve. The outer tube 902, which includes a telescoping section 906, expands vertically to facilitate dispensing of the medication container 20. The dispensing tube 710 also includes a pin at a bottom of the inner tube 900 that acts as a floor for the medication container 20. A pin actuator 730, which is communicatively coupled to the processor 16, is located within the dispensing tube 710 and controls the movement of the pin.

Figure 9A:
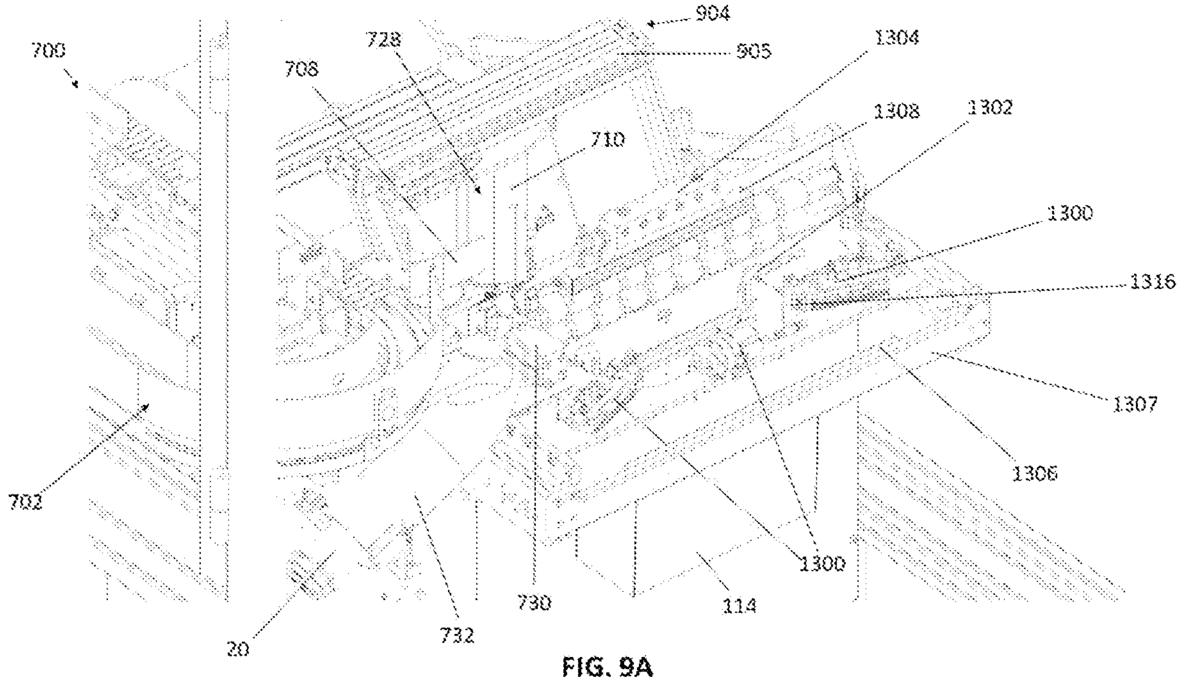
FIG. 9A shows a view of the packaging apparatus and the dispensing tube without a medication container, according to an example embodiment of the present disclosure.
Figure 9B:
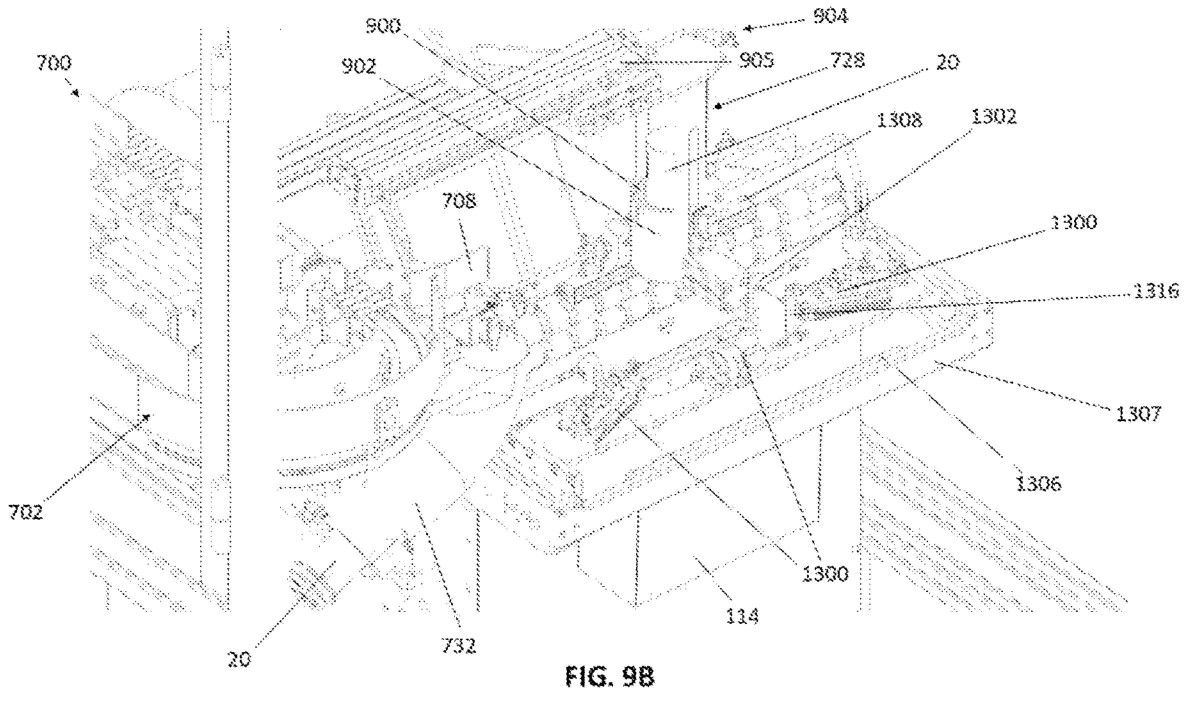
FIG. 9B shows a view of the packaging apparatus and the dispensing tube with a medication container in it prior to the telescoping section being expanded, according to an example embodiment of the present disclosure.
Figure 9C:
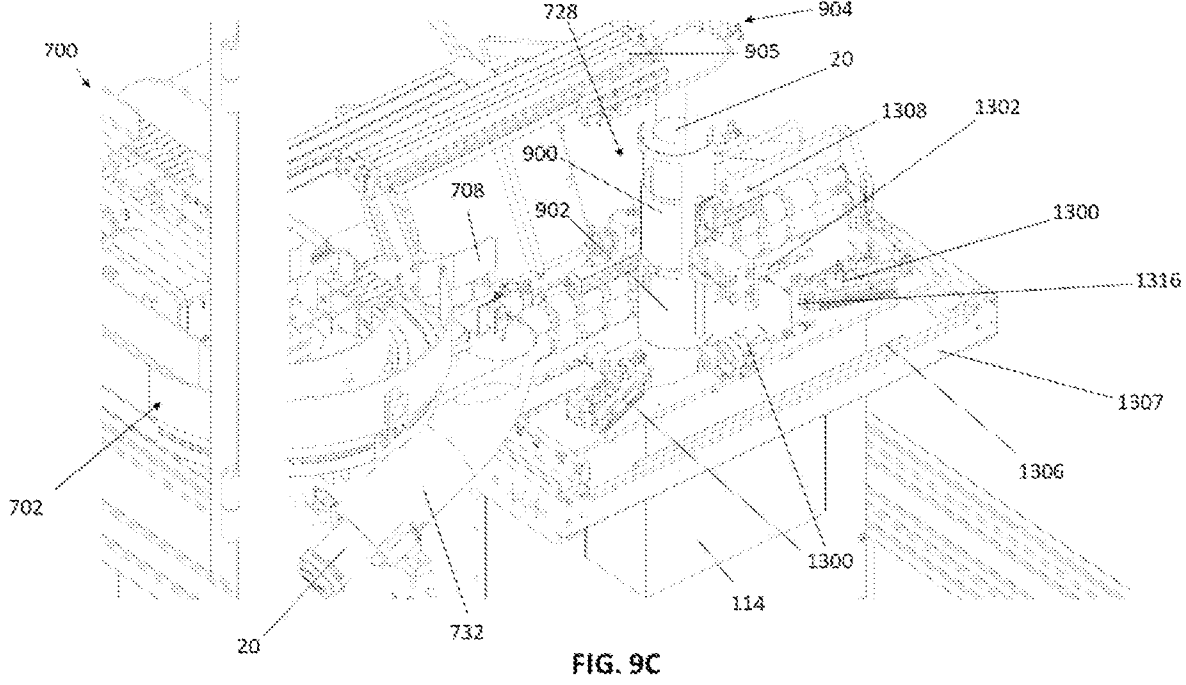
FIG. 9C shows a view of the packaging apparatus and the dispensing tube with a medication container in it with an expanded telescoping section, according to an example embodiment of the present disclosure.

When the medication container 20 is deposited into the dispensing tube 710, the processor 16 relays movement instructions to the controller 18, which directs the lateral movement section 904 to transfer the medication container 20 to a receptacle 602 that is ready to be filled. The lateral movement section 904 can move the medication container 20 contained within the dispensing tube 710 from the output transport mechanism 704 to the receptacle 602, as shown in FIGS. 9A-9C.

After the processor 16 determines that the dispensing tube 710 has arrived at a location directly above an opened receptacle 602, lateral movement of the inner tube 900 stops. As described below, the opened receptacle 602 may be a bag 114 in the packaging apparatus 106. As shown in FIG. 9C, the telescoping section 906 of the outer tube 902 enveloping the inner tube 900 expands vertically downward towards the receptacle 602 to ensure that the medication container 20 is contained within the receptacle prior to dropping the medication container 20. When the telescoping section 906 of the outer tube 902 is fully extended, the pin actuator 730 releases the pin and the medication container 20 falls into the receptacle 602. Though the illustrated embodiments utilize gravity to drop the medication container 20 within the receptacle, other methods known to a person having an ordinary skill in the art may be utilized.

Packaging Apparatus Embodiment

After both the medication documentation 10 and the medication container 20 are obtained and confirmed to match the patient information, the packaging process begins. FIGS. 10A-15 illustrate the packaging process with the packaging apparatus 106, according to an example embodiment of the present disclosure. The medication documentation 10 and accompanying medication container 20 can be packaged into a receptacle 602 of any kind. This may include bags, boxes, pouches, bins, packages, or containers. In some embodiments, the packaging process may take less than five seconds.

In illustrated embodiments, the receptacles 602 filled by the packaging apparatus 106 are bags 114. The bags 114 can be individual pre-made bags or a plurality of bags that are attached to one another (i.e., a preformed length of bags). Additionally, a pre-made plurality of bags that are affixed to one another may be wound up into a roll or folded into a predetermined shape. The packaging apparatus 106 may accommodate both kinds of configurations. In illustrated embodiments, the bags 114 are wound up into a roll.

Figure 10A:
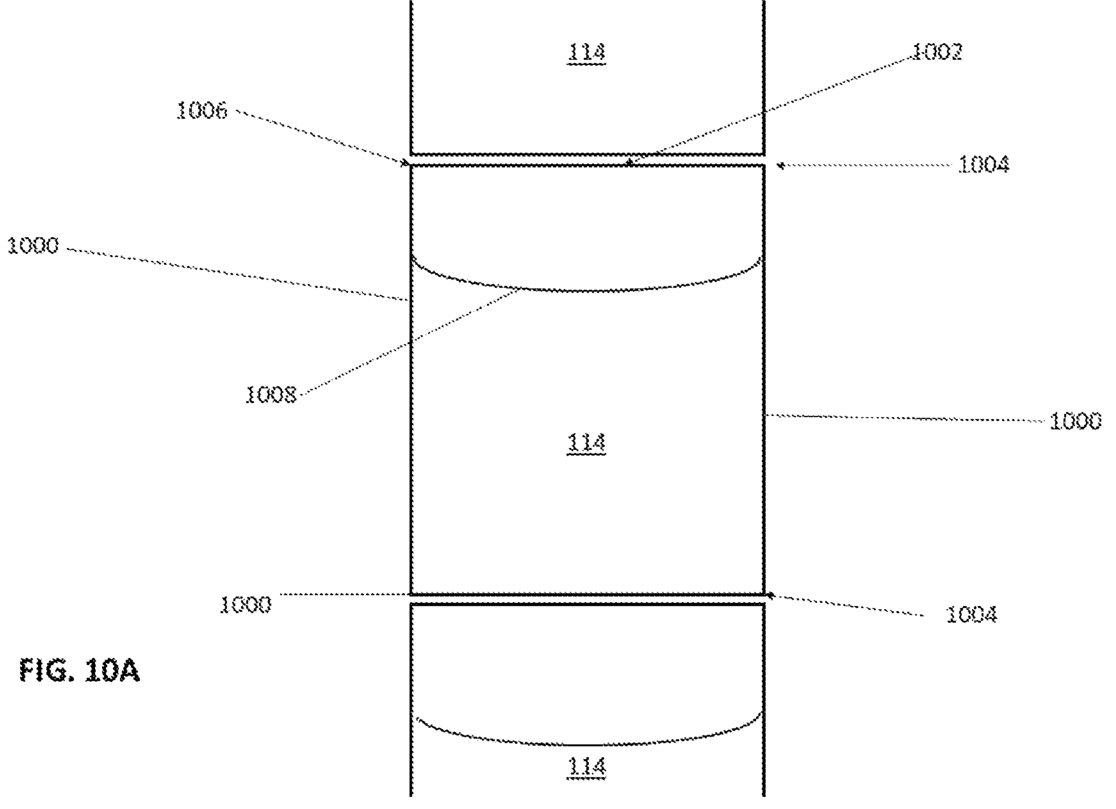
FIG. 10A shows a front view of pre-attached bags that are no longer connected, according to an example embodiment of the present disclosure.
Figure 10B:
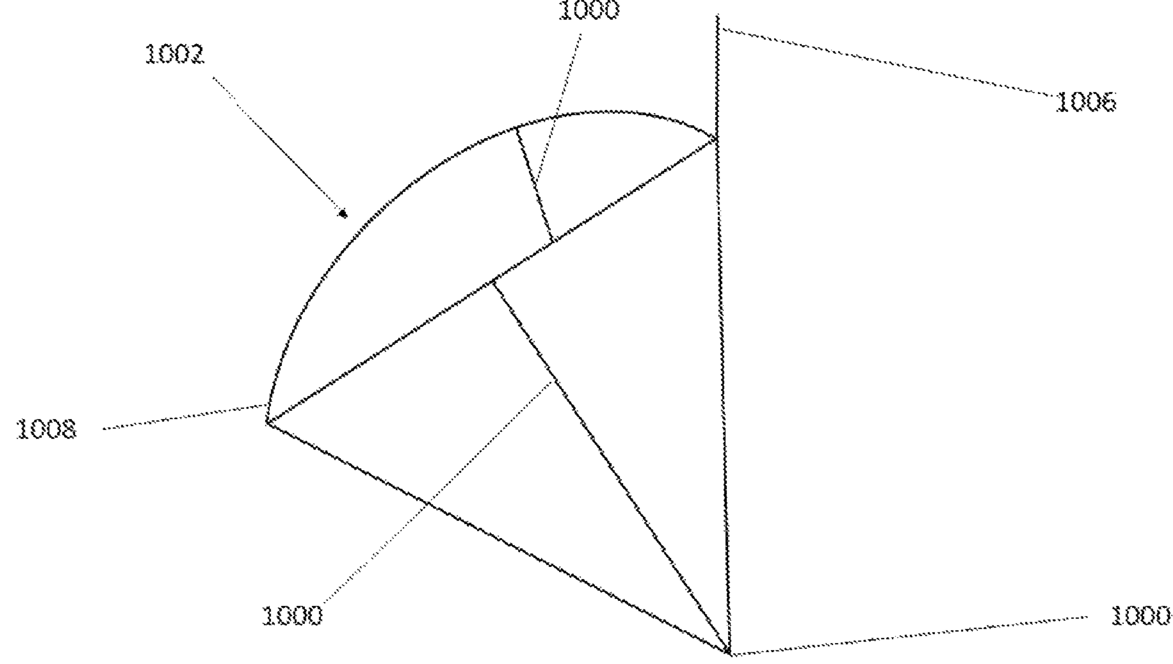
FIG. 10B shows a side view of a bag, according to an example embodiment of the present disclosure.

It should be appreciated that the bags 114 disclosed herein and illustrated in FIGS. 10A and 10B are exemplary. The packaging apparatus 106 can package any bag that includes at least three edges 1000 that are already sealed together. The remaining edge that is unsealed is known as an inflation edge 1002. The volume of the bags 114 utilized in the packaging apparatus 106 is predetermined, though the packaging apparatus 106 may be manually altered to accommodate multiple different-sized bags 114, as described below.

In the illustrated embodiment, the bags 114 are made of a polymer such as ethylene. In some embodiments, the bags 114 can be made of high-density polyethylene ("HDPE"), low-density polyethylene ("LDPE"), or linear low-density polyethylene ("LLDPE"). In yet other embodiments, the bags 114 are made of paper or a paper-based compound. There is no coating on the interior on the bags 114.

The bags 114, as shown in from a front view in FIG. 10A and a side view in FIG. 10B, may also contain perforations 1004. In illustrated embodiments, a back side 1006 of the inflation edge 1002 of the leading bag 114 may be perforated and attached to a bottom edge of another bag in the plurality of bags 114. In this embodiment, a front side 1008 of the inflation edge 1002 of the leading bag 114 is not attached to another bag. In other embodiments, the perforations 1004 may be located at different locations on the leading bag 114. Some perforations 1004 may extend perpendicularly from the inflation edge 1002 of the leading bag 114. Bags 114 may also have smaller holes to ensure that the leading bag 114 does not contain excess air when fully sealed. It should be appreciated that the perforations 1004 and other bag holes identified in the application are exemplary and other perforations 1004 and other bag configurations may be utilized with other embodiments of the packaging apparatus 106.

Figure 11:
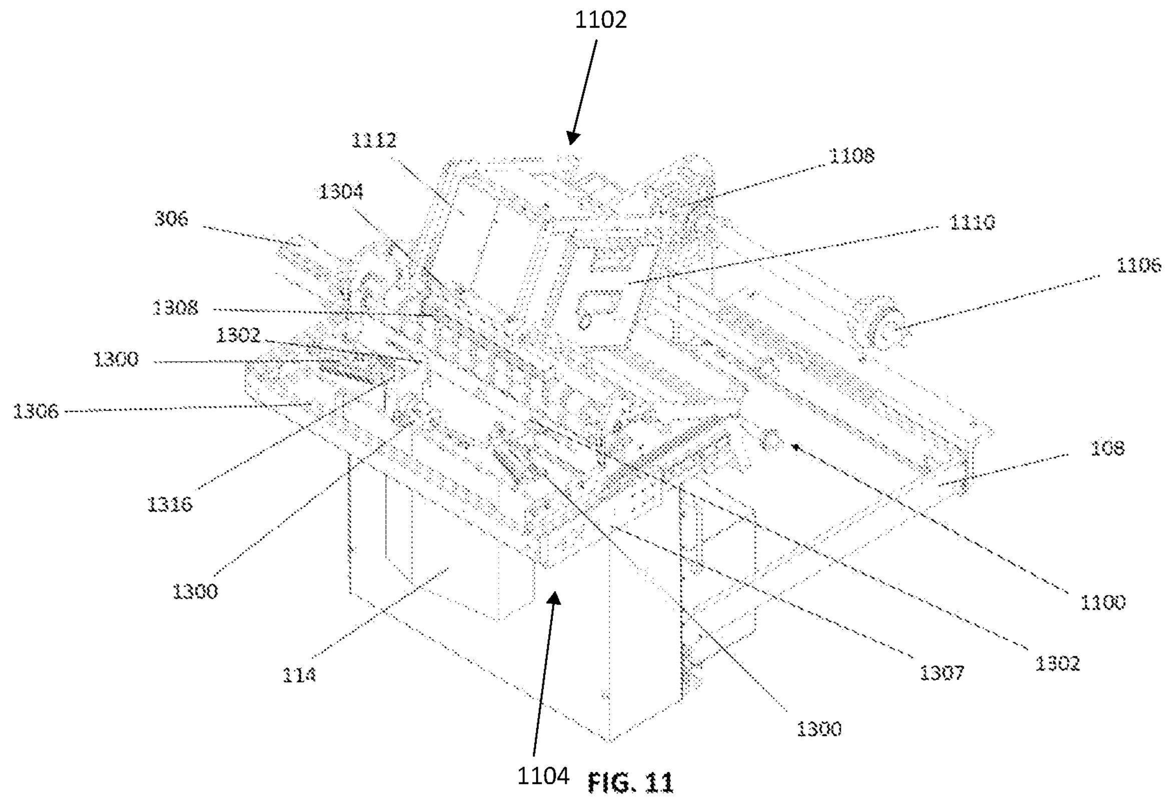
FIG. 11 shows an isometric view of the packaging apparatus, according to an example embodiment of the present disclosure.

Referring now to FIG. 11, the packaging apparatus 106 includes a bag transport mechanism 1100, a printing station 1102, and a loading station 1104. The method for packaging medication documentation 10 and medication containers 20 at the packaging apparatus 106 includes feeding a leading bag 114 to the printing station 1102, printing patient information onto the leading bag 114, transporting the leading bag 114 to a loading station 1104, opening the leading bag 114, engaging the leading bag 114, filling the leading bag 114 with medication documentation 10 and at least one medication container 20, stretching the leading bag 114 taut, and sealing the leading bag 114.

The bag transport mechanism 1100 is affixed to the main frame 108, configured to receive a plurality of bags, and moves a leading bag 114 through the entirety of the packaging apparatus 106 system. In some embodiments, the bag transport mechanism 1100 is a plurality of rollers. The rollers 1100 are spaced in a configuration that creates tension on the plurality of bags 114. In other embodiments, the bag transport mechanism 1100 may be a conveyor track, belt conveyor system, or a dial machine indexer. The bag transport mechanism 1100 cooperates with a motor 306 to transport the leading bag 114 to various stations, such as the printing station 1102 and the loading station 1104. For the purposes of this application, only the roller embodiment is described.

In an illustrated embodiment, the bags 114 are affixed to one another in a roll. To allow the bag transport mechanism 1100 to operate on the roll, the roll is placed on a freely rotatable dowel 1106 where a leading bag 114 of the roll is fed through the plurality of rollers 1100 in the bag transport mechanism 1100. Once the processor 16, via the controller 18, transmits movement instructions to the motor 306, the rollers 1100 spin and create tension on the roll, pulling the bags 114 through the rollers 1100 to continue moving throughout the packaging apparatus 106, as described further below.

In this instance, to keep the bag transport mechanism 1100 from moving the plurality of bags 114 too quickly, a clutch 1108 is placed around the dowel 1106 to prevent the rollers 1100 from spinning loosely. The clutch 1108 maintains the bag roll and leading bag 114 in the correct position. The clutch 1108 consists of springs which compress to create friction on the dowel 1106 thereby stopping the movement of the rollers 1100 entirely when activated.

Figure 12:
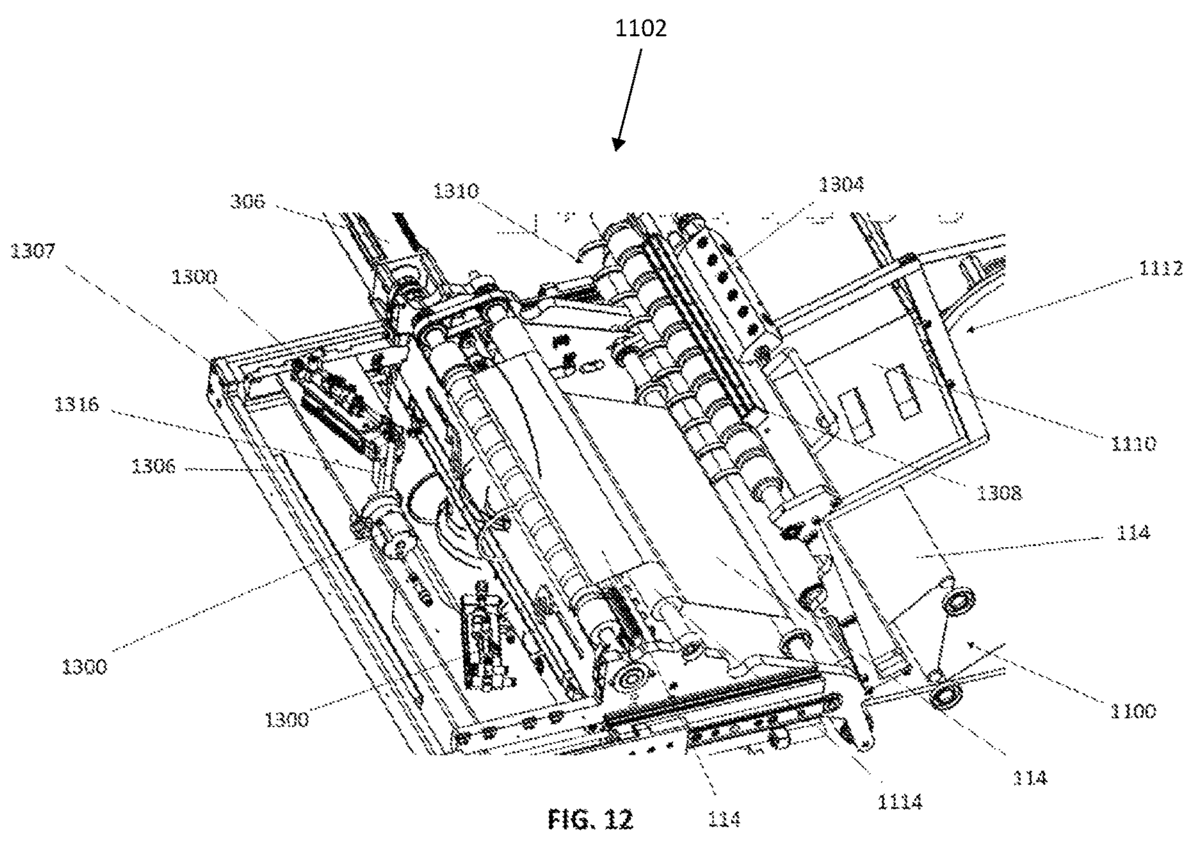
FIG. 12 shows a top view of the printing station and loading station in the packaging apparatus, according to an example embodiment of the present disclosure.

Next, the bag transport mechanism 1100 delivers a leading bag 114 to a printing station 1102 shown in FIG. 12. The printing station 1102 includes a thermal transfer printer 1110, a pivotable thermal transfer printer frame 1112, and a silicone roller 1114. A thermal transfer printer 1110 is contained within a pivotable thermal transfer printer frame 1112, which prints patient information directly onto the leading bag 114. The patient information to be printed onto the leading bag 114 includes a bar code 11 that matches the patient information in the fulfillment database 14. The pivotable thermal transfer printer frame 1112 can be opened or closed so that an operator may access the bag transport mechanism 1100 or other component inside the packaging apparatus 106.

The thermal transfer printer 1110 is operated by the controller 18. The controller 18 employs modular printing systems to transmit and receive print commands. This modular printing system can be customized to appropriately control the packaging apparatus 106. The custom modular printing system may be built using pre-existing modular printing systems such as Linux CUPS.

At the printing station 1102, the front side 1008 of the leading bag 114 is pulled taut by the rollers 1100 in the bag transport mechanism 1100. The leading bag 114 is woven over some rollers and under other rollers within the bag transport mechanism 1100 to create tension. A sensor 301 located within the printing station 1102 communicates with the application server 300 to notify the processor 16 that the leading bag 114 is ready for printing. The processor 16 then transmits movement instructions to the controller 18 which actuates the thermal transfer printer 1110 to print onto the leading bag 114. The thermal transfer printer 1110 prints designs on the front side 1008 of the leading bag 114 that is resting on the silicone roller 1114. The processor 16 may only transmit the movement instructions after the processor 16 receives an indication that a corresponding medications container is ready to be dispensed from the infeed loop apparatus 104. In such an embodiment, the processor 16 may cause the thermal transfer printer 1110 to print at least some of the patient information on the bag 114 while causing the printer 400 of the medication documentation preparation apparatus 102 to print the medication documentation 10 from the same patient information.

Once complete, the processor 16 transmits movement instructions to the controller 18 and the leading bag 114 is transported to a loading station 1104 by the bag transport mechanism 1100, which is powered by the motor 306.

Figure 13:
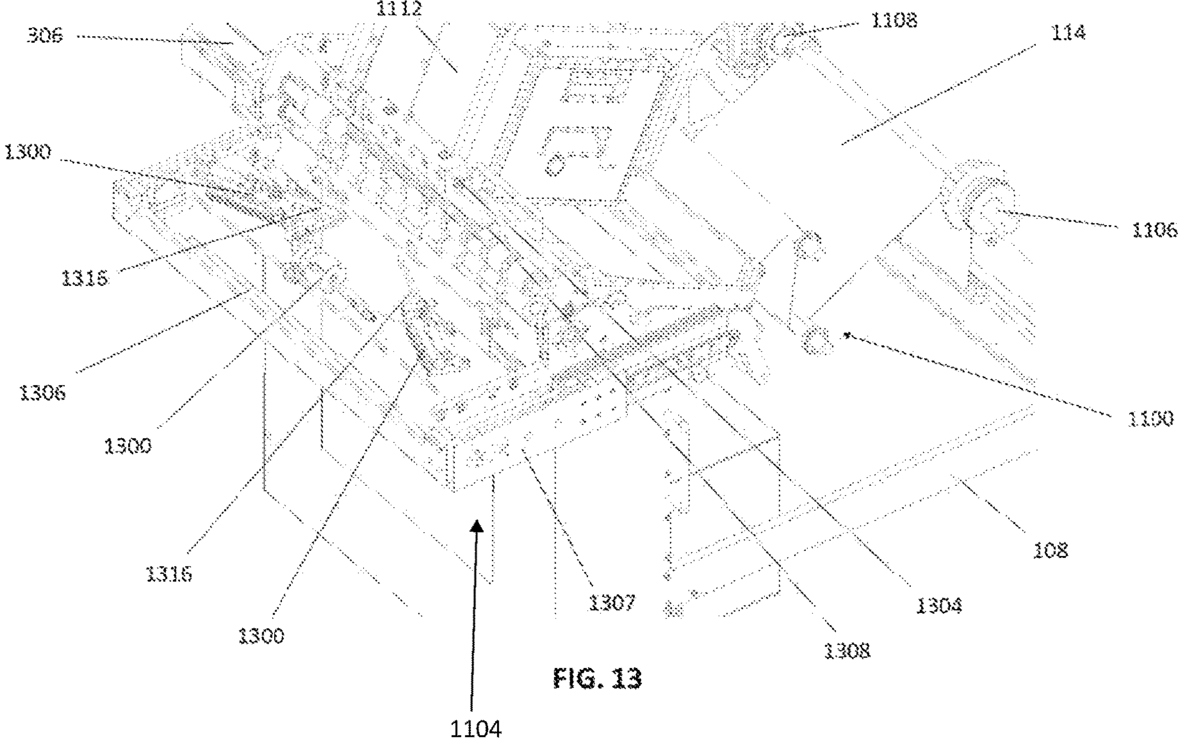
FIG. 13 shows an isometric view of the bag transport mechanism and loading station with a closed bag, according to an example embodiment of the present disclosure.
Figure 14:
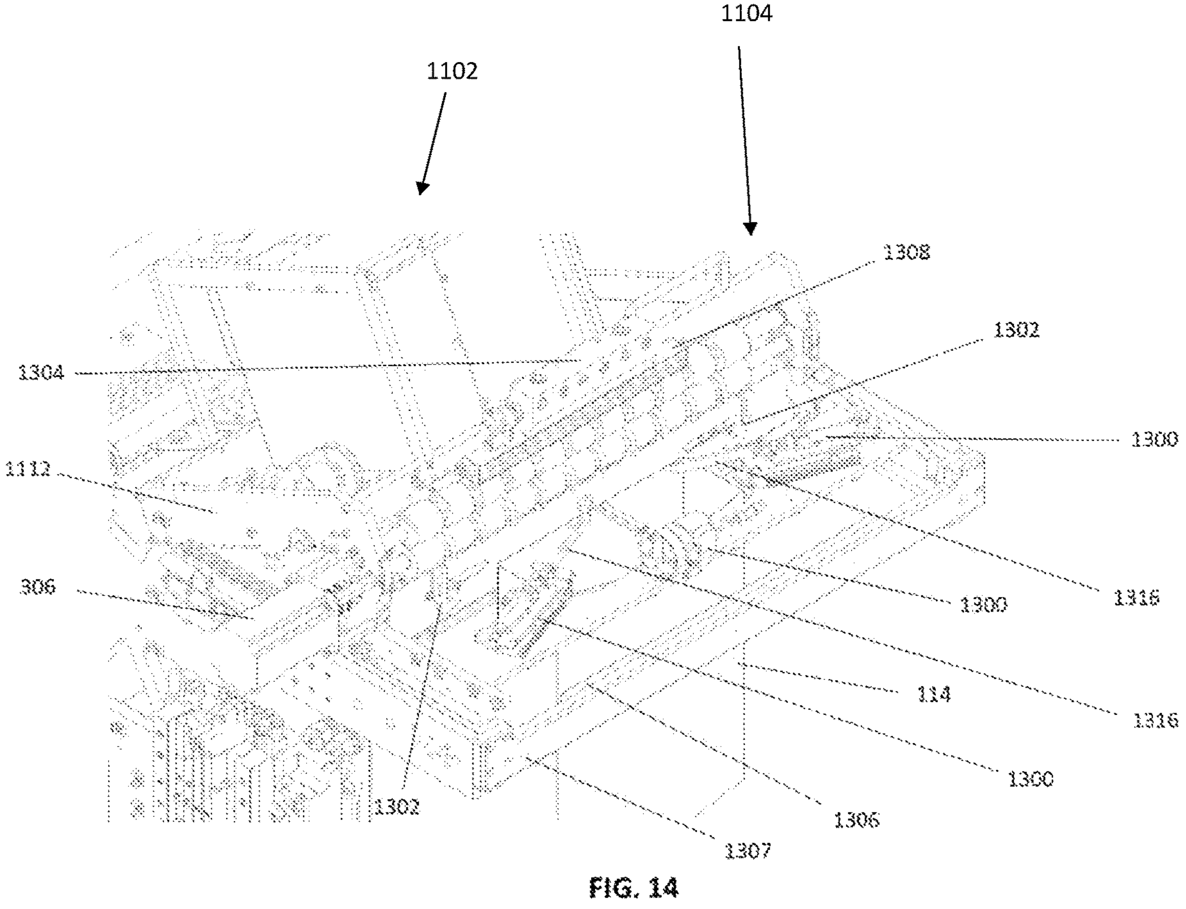
FIG. 14 shows an isometric view of the loading station with an open bag in the packaging apparatus, according to an example embodiment of the present disclosure.
Figure 15:
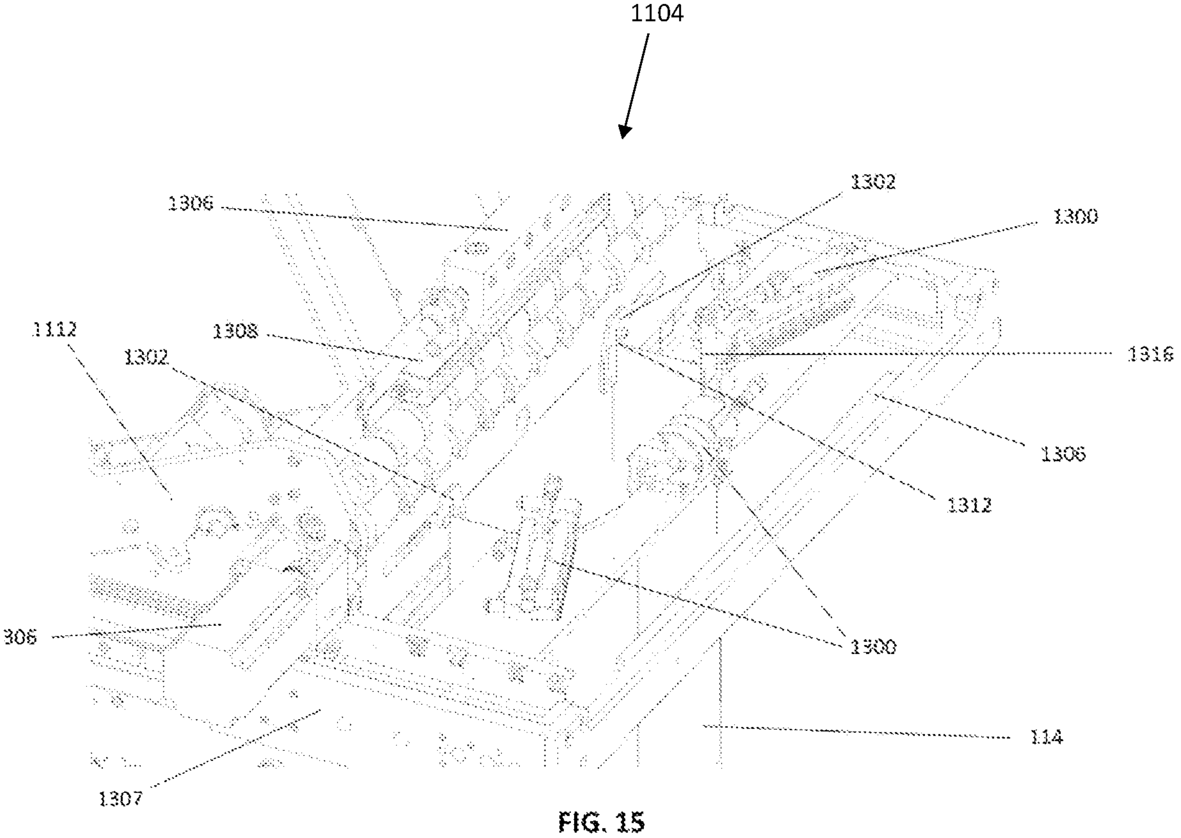
FIG. 15 shows a close-up view of the loading station with an open bag in the packaging apparatus, according to an example embodiment of the present disclosure.

As shown in FIGS. 13-15, the loading station 1104 includes at least a first, a second, and a third articulable finger 1300, at least a first and a second bag gripper 1302, an air knife 1304, a sealing mechanism 1306, and an outer packaging frame 1307. In an illustrated embodiment, the loading station 1104 also includes a static eliminating mechanism 1308. There is a sensor 301 located between the first and second bag grippers 1302 that detects when the leading bag 114 has arrived and is properly located in the loading station 1104. The sensor 301 communicates with the processor 16 when the leading bag 114 is in a proper position, which causes the processor 16 to transmit movement instructions to the controller 18 and the accompanying motor 306 to begin the loading process.

In the illustrated embodiments, at the loading station 1104, the leading bag 114 is positioned vertically so as to have an inflation edge 1002 exposed directly beneath an air knife 1304, though this configuration may vary in other embodiments. Angled bag fingers 1310 wrapped around a roller on the bag transport mechanism 1100 allow for the leading bag 114 to fall vertical. Compressed air is then blown by the air knife 1304 towards the inflation edge 1002 of the leading bag 114. In one embodiment, the leading bag 114 is perforated, so that when compressed air at a high enough pressure is blown tangential to the inflation edge 1002, the perforations 1004 along the inflation edge 1002 break and the leading bag 114 is opened. In another embodiment, a back side 1006 of the leading bag 114 along the inflation edge 1002 is perforated and attached to other bags while a front side 1008 of the leading bag 114 along the inflation edge 1002 is not attached to any other bag. In this instance, the compressed air, blown by the air knife 1304, when angled correctly, blows the front side 1008 of the leading bag 114 away from the back side 1006 causing the bag to substantially open as illustrated by FIG. 10B.

As many bags 114 are comprised of materials conducive to static electricity, even when the air knife 1304 blows over the leading bag 114, the edges 1000 of the leading bag 114 may not naturally open if the leading bag 114 is charged with static electricity as the edges 1000 may be attracted to one another. To mitigate this problem, a static eliminating mechanism 1308 is located within the flow path of the compressed air, between the air knife 1304 and the leading bag 114. In the illustrated embodiments, the static eliminating mechanism 1308 is an ionizing bar. The ionizing bar adds positive and negative ions to the air flow, which neutralizes any static electricity that has built up on the leading bag 114. As a result, the front side 1008 of the inflation edge 1002 and the back side 1006 of the inflation edge 1002 of the leading bag 114 are no longer attracted to one another and the compressed air flow substantially opens the bag as illustrated by block 228 in FIG. 2D.

A sensor 301 is used to detect when the leading bag 114 has a large enough opening to insert the medication documentation 10 and medication container 20 into the leading bag 114. The sensor 301 communicates with the processor 16, which determines when the leading bag 14 is considered open. After the processor 16, determines that the leading bag 114 is open, the processor 16 causes the first and second bag grippers 1302 to engage with the opened leading bag 114. Each bag gripper 1302 has two gripper appendages 1312 connected to one another and pointed perpendicularly away from one another so as to form an L-shape. The bag grippers 1302 rotate about an end point 1314 to allow the bag grippers 1302 to pivot into the bag 114. The first bag gripper 1302, located on a left side of the leading bag 114, rotates clockwise into the leading bag 114 until one gripper appendage 1312 is parallel to the inflation edge 1002 of the leading bag 114 and the other gripper appendage 1312 is perpendicular to the inflation edge 1002 of the leading bag 114. The second bag gripper, located on a right side of the leading bag 114, rotates counterclockwise into the leading bag 114 until one gripper appendage 1312 is parallel to the inflation edge 1002 of the leading bag 114 and the other gripper appendage 1312 is perpendicular to the inflation edge 1002 of the leading bag 114. Both bag grippers 1302 move simultaneously and are connected to the same motor 306.

After the bag grippers 1302 have engaged the leading bag 114, the articulable fingers 1300 then engage the leading bag 114. Due to the rapid speed of the packaging apparatus 106, the bag gripper 1302 engagement and the articulable finger 1300 engagement appear to be nearly simultaneous.

The first, second, and third articulable fingers 1300 are located on the outer packaging frame 1307, which is positioned near the front side 1008 of the leading bag 114. The fingers 1300 are used to hold the leading bag 114 open. Each finger 1300 includes a finger appendage 1316 that can move between an open and a closed position. When closed, as shown in FIG. 12, the finger appendage 1316 rests perpendicular to the inflation edge 1002 of the leading bag 114. When opened, as shown in FIG. 13, the finger appendage 1316 rests parallel to the inflation edge 1002 of the leading bag 114. The finger appendage 1316 position is altered by an actuator 308 that is connected to the fingers 1300 and communicatively coupled with the processor 16. In an illustrated embodiment, the actuator 308 is a pneumatic valve. When given movement instructions from the processor 16, a rod on the pneumatic valve retracts to move the finger appendage 1316. When the rod retracts, the finger appendage 1316 automatically drops down into the closed position. The finger appendage 1316 is farther from the back side 1006 of the leading bag 114 in a closed position. As a result, the closed position puts tension on the leading bag 114 causing the bag to be pulled taut along the back side 1006 of the inflation edge 1002.

When the leading bag 114 is opened by the air knife 1304 (block 228), the finger appendages 1316 are in the open position. A sensor 301 communicatively coupled to the processor 16 relays a signal to the processor 16 indicated that the leading bag 114 is sufficiently opened. The processor 16 then transmits movement instructions to the actuator 308 to engage the fingers 1300 with the leading bag 114. The fingers 1300 operate at the same time as one another. Once all fingers 1300 engage the leading bag 114 and all finger appendages 1316 are in the closed position and a nearby sensor 301 confirms and relays this information to the processor 16, the processor 16 transmits movement instructions to the controller 18 and the outer packaging frame 1307 is moved away from the leading bag 114 by the motor 306. Because of this motion, the fingers 1300 pull the leading bag 114 open further. The leading bag 114 has an opening defined by the inflation edge 1002 that is pentagonal. It will be appreciated that this method of opening the bag is purely exemplary and other methods may be known to a person having ordinary skill in the art.

The leading bag 114 is then filled with the medication documentation 10 and medication container 20 corresponding to the patient information. As described above, the corresponding medication documentation 10 is brought and deposited into the leading bag 114 by the gantry assembly 406. As described above, the corresponding medication container 20 is brought and deposited into the leading bag 114 by the dispensing tube 710.

To prepare for the sealing process, after the leading bag 114 is filled with medication documentation 10 and the medication container 20, the processor 16 transmits movement instructions to the motor 306 connected to the bag grippers 1302. While the bag grippers 1302 are still engaged with the leading bag 114, the motor 306 pulls the bag grippers 1302 horizontally in a direction away from the leading bag 114. The first bag gripper 1302 is pulled to a left side of the packaging apparatus 106 and the second bag gripper 1302 is pulled to a right side of the packaging apparatus 106. This causes the leading bag 114 to be stretched and for the front side 1008 and back side 1006 of the leading bag 114 to be brought close together for sealing.

The bag grippers 1302 are pulled away to a predefined distance depending on the size of the leading bag 114. This distance can be manually altered by a switch located within the packaging apparatus 106. For instance, in some embodiments, the inflation edge 1002 of the leading bag 114 may be twelve inches. In other embodiments, the inflation edge 1002 of the leading bag 114 may be fourteen inches.

Once the first and second bag grippers 1302 have been pulled away from one another, the back side 1006 of the leading bag 114 comprises a straight line that is parallel to the sealing mechanism 1306. The sealing mechanism 1306 fuses the front side 1008 and back side 1006 of the leading bag 114 so that the leading bag 114 is completely sealed from any outside elements. In the illustrated embodiments, the sealing mechanism 1306 is a heat seal bar. In other embodiments, the sealing mechanism 1306 may be a vacuum sealer, cold sealer, or other heat sealer. In yet other embodiments, an element may be added to the leading bag 114 by the sealing mechanism 1306 to seal the leading bag 114. This may include adding a tie, clasp, clip, or other mating device. For the purposes of this application, only the heat seal bar embodiment will be described.

The heat seal bar 1306 is a metal bar that is heated by a heating transformer. The heating transformer may be located at the bottom of the medication bagger system 100 or in another location so as not to impede on any of the packaging apparatus 106 operations, the infeed loop apparatus 104 operations, or medication documentation preparation apparatus 102 operations. The heat seal bar 1306 is raised to at least to a temperature at which the material of the leading bag 114 melts.

The heat seal bar 1306 is placed on the outer packaging frame 1307 controlled by pneumatic actuators 308. When the leading bag 114 has been pulled taut by the bag grippers 1302, the finger appendages 1316 return to an open position and disengage the leading bag 114. The outer packaging frame 1307 then moves the heat seal bar 1306 towards the leading bag 114 until the heat seal bar 1306 mates with a silicone seal pad 1318 located behind the leading bag 114 on the main frame 108. The silicone seal pad 1318 is able to withstand the high temperature, whereas the material on the leading bag 114, as described above, usually a plastic, melts on both the front side 1008 and back side 1006 of the leading bag 114. Once the front side 1008 and back side 1006 of the leading bag 114 melt, the plastics fuse under pressure from the heat seal bar 1306 and silicone seal pad 1318. The bag grippers 1302 disengage with the leading bag 114 as the heat sealing process begins. The heat sealing process takes approximately 250 milliseconds, though other types of sealing processes may vary in duration.

Depending on the type of bag 114 used in the packaging apparatus 106, it may be necessary to remove excess air from the leading bag 114 prior to sealing. If the leading bag has any holes, such as a pre-made hole punch, it is not necessary to remove excess air from the leading bag 114, as the leading bag 114 can release air through the holes. In instances where the leading bag 114 would not have any holes after sealing, foam pads may be attached beneath the heat seal bar 1306 on the outer packaging frame 1307, as well as beneath the silicone seal pad 1318 to push air out as the sealing process occurs. The slight pressure from the foam pads pushes excess air out so that the leading bag 114 when sealed is not too inflated so as to risk puncture.

During the sealing process, as the heat seal bar 1306 mates with the silicone seal pad 1318, the controller 18 is configured to provide movement instructions to the motor 306 operating the bag transport mechanism 1100. The motor 306 is configured to reverse index in the direction of pulling the leading bag 114 back towards the printing station 1102. As the leading bag 114 is held in place by the heat seal bar 1306 and silicone seal pad 1318, perforations 1004 on the inflation edge 1002 of the leading bag 114 break from the applied force of the reverse indexing. Depending on the material of the leading bag 114, the motor 306 may need to reverse index.

Nevertheless, once the perforations 1004 break, the outer packaging frame 1307 moves the heat seal bar 1306 away from the silicone seal pad 1318, the leading bag 114 falls. In some embodiments, the leading bag 114 falls onto a conveyor and be processed by an operator at the pharmacy fulfillment center. In other embodiments, the leading bag 114 remains in the dispense area 600 until an operator removes it.

The methods described above may be performed in any order and the methods described above may include more, fewer, or other steps.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medication documentation preparation apparatus for a medication bagger system, the medication documentation preparation apparatus comprising:
- a tray configured to receive medication documentation;
- at least two rollers positioned next to each other to define a slit therebetween;
- a gantry assembly configured to move between two positions, the gantry assembly including:
  - a first arm,
  - a second arm connected to the first arm,
  - a pusher connected to an end of the second arm, the pusher having a width that is less than the slit formed between the at least two rollers, and
  - a first gantry gripper and a second gantry gripper that are each configured to engage the medication documentation; and
- a processor communicatively coupled to at least one motor for controlling a positioning of the gantry assembly, movement of the first arm, movement of the second arm, and at least one actuator for controlling engagement of the first gantry gripper and the second gantry gripper, the processor configured to:
  - (a) cause the at least one motor to move the gantry assembly to a position that is aligned with the tray,
  - (b) cause the at least one motor to move the first arm causing the pusher to push the medication documentation into the slit between the at least two rollers to fold the medication documentation,
  - (c) cause the at least one actuator to engage the first and second gantry grippers with the folded medication documentation,
  - (d) cause the at least one motor to move the first arm away from the at least two rollers,
  - (e) cause the at least one motor to move the gantry assembly to a position that is aligned with a receptacle,
  - (f) cause the at least one motor to move the first arm to a dispense area, and
  - (g) cause the at least one motor to move the second arm to the dispense area, causing the medication documentation to be dispensed into the receptacle.

2. The medication documentation preparation apparatus of claim 1, further comprising a bar code scanner configured to scan a bar code on at least one page of the medication documentation, wherein the processor is further configured to compare patient information from the scanned bar code to patient information in a fulfillment database.

3. The medication documentation preparation apparatus of claim 2, wherein the processor is further configured to cause the at least one motor to move the first arm to cause the pusher to push the medication documentation into the slit between the at least two rollers to fold the medication documentation in half when the scanned patient information matches the patient information in the fulfillment database.

4. The medication documentation preparation apparatus of claim 2, wherein the processor is further configured to skip (c) to (g) when the scanned patient information does not match the patient information in the fulfillment database.

5. The medication documentation preparation apparatus of claim 4, wherein the processor is further configured to cause (i) the at least one motor to move the first arm to an intermediate position, or (ii) the at least one motor to move the first arm to a dispense position to push the medication documentation through the slit into a discard tray.

6. The medication documentation preparation apparatus of claim 4, wherein the processor is further configured to generate an alert.

7. The medication documentation preparation apparatus of claim 2, wherein the processor is further configured to skip (c) to (g) when the scanned patient information is indicative that the bar code cannot be read.

8. The medication documentation preparation apparatus of claim 2, wherein the bar code scanner is configured to read a first bar code located on a first page and a second bar code location on a last page of the medication documentation.

9. The medication documentation preparation apparatus of claim 1, further comprising a second bar code scanner configured to scan a bar code on the receptacle, wherein the processor is further configured to compare scanned patient information from the scanned bar code on the medication documentation to patient information from the second bar code scanner.

10. The medication documentation preparation apparatus of claim 9, wherein the processor is further configured to cause the at least one motor to move the first arm to cause the pusher to push the medication documentation into the slit between the at least two rollers to fold the medication documentation in half when the scanned patient information matches the patient information in a fulfillment database.

11. The medication documentation preparation apparatus of claim 9, wherein the processor is further configured to skip (c) to (g) when the scanned patient information does not match the patient information in a fulfillment database.

12. The medication documentation preparation apparatus of claim 11, wherein the processor is further configured to cause (i) the at least one motor to move the first arm to an intermediate position, or (ii) the at least one motor to move the first arm to a dispense position to push the medication documentation through the slit into a discard tray.

13. The medication documentation preparation apparatus of claim 11, wherein the processor is further configured to generate an alert.

14. The medication documentation preparation apparatus of claim 9, wherein the processor is further configured to skip (c) to (g) when the scanned patient information is indicative that a bar code cannot be read.

15. The medication documentation preparation apparatus of claim 1, wherein the tray includes at least two sidewalls and at least one stopper for aligning a center of the medication documentation over the at least two rollers.

16. The medication documentation preparation apparatus of claim 1, further comprising:

a printer configured to print the medication documentation; and a transporter configured to move the medication documentation from the printer to the tray after receiving a signal from the processor.

17. The medication documentation preparation apparatus of claim 16, wherein the transporter includes at least two paper rollers actuated by a roller motor.

18. The medication documentation preparation apparatus of claim 1, further comprising a third gantry gripper and a fourth gantry gripper that are each configured to engage the medication documentation.

19. The medication documentation preparation apparatus of claim 1, wherein the processor is further configured to cause a medication container to be dispensed into a receptacle after the medication documentation is dispensed.

20. The medication documentation preparation apparatus of claim 1, wherein the tray includes a window located in a middle section of the tray and the at least two rollers are located within or beneath the window of the tray.

* * * * *